(12) United States Patent
Amano et al.

(10) Patent No.: US 6,331,159 B1
(45) Date of Patent: *Dec. 18, 2001

(54) DEVICE FOR MEASURING PHYSIOLOGICAL STATE

(75) Inventors: Kazuhiko Amano, Suwa; Kazuo Uebaba, Yokohama; Hitoshi Ishiyama, Toride, all of (JP)

(73) Assignee: Seiko Epson Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/636,775

(22) Filed: Aug. 11, 2000

Related U.S. Application Data

(63) Continuation of application No. 08/860,579, filed as application No. PCT/JP96/03211 on Nov. 1, 1996.

(30) Foreign Application Priority Data

Nov. 1, 1995 (JP) .................................. 7-285411
Nov. 1, 1995 (JP) .................................. 7-285412

(51) Int. Cl.$^7$ ................................ A61B 5/00; A61B 5/02
(52) U.S. Cl. .......................... 600/300; 600/508; 600/500
(58) Field of Search .................................. 600/300, 301, 600/481, 486, 500, 508, 423; 128/898, 900

(56) References Cited

U.S. PATENT DOCUMENTS 6,171,242 * 1/2001 Amano et al. ................... 600/423

* cited by examiner

Primary Examiner—John P. Lacyk
Assistant Examiner—Michael Astorino
(74) Attorney, Agent, or Firm—Mark P. Watson

(57) ABSTRACT

A non-invasive device for evaluating circulatory state parameters, and specifically, a pulsewave analysis device capable of evaluation by separating blood vessel compliance and blood vessel resistance into central and peripheral components of the arterial system is provided. Microcomputer 4 detects the waveform at a test subject's radius artery via pulsewave detector 1, and uptakes the stroke volume in the test subject which is measured by a stroke-volume measurer. Next, based on the measured stroke volume, microcomputer 4 adjusts the values of each element in a lumped five parameter model made up of an electrical circuit which models the arterial system from the center to the periphery of the body, so that the response waveform obtained when an electric signal corresponding to the pressure waveform at the proximal portion of the aorta in a test subject is provided to the electric circuit coincides with the waveform at the radius artery. Microcomputer 4 then outputs the thus-obtained values of each element as circulatory state parameters. In addition, microcomputer 4 calculates the diastolic pressure value, systolic pressure value and pulse waveform at the proximal portion of the aorta from the values of each element, and outputs the calculated result to output device 6.

4 Claims, 24 Drawing Sheets

$V_1$: AORTIC PRESSURE
$V_p$: RADIUS ARTERY PRESSURE e: PRESSURE IN THE LEFT CARDIAC VENTRICLE
$V_1$: AORTIC PRESSURE
$V_p$: RADIUS ARTERY PRESSURE

SOLID LINE: MEASURED WAVEFORM OF RADIUS ARTERY
(SUMMED AVERAGE)
DASHED LINE: CALCULATED WAVEFORM $R_c = 88.588 \,(\text{dyn}\cdot\text{s}/\text{cm}^5)$  $C_c = 12.066 \times 10^{-4} \,(\text{cm}^5/\text{dyn})$
$R_p = 1453.953 \,(\text{dyn}\cdot\text{s}/\text{cm}^5)$  $C = 1.207 \times 10^{-4} \,(\text{cm}^5/\text{dyn})$
$L = 15.542 \,(\text{dyn}\cdot\text{s}^2/\text{cm}^5)$  $SV = 72.0 \,(\text{cc}/\text{beat})$
$W_s = 65.3 \,(\text{J}/\text{min})$ SOLID LINE: PRESSURE WAVEFORM AT THE RADIUS ARTERY
(72.7/115.9mmHg)
DASHED LINE: PRESSURE WAVEFORM AT THE AORTA
(76.8/111.4mmHg)

$R_c = 28.103 \, (\text{dyn} \cdot \text{s}/\text{cm}^5)$  $C_c = 8.00 \times 10^{-4} \, (\text{cm}^5/\text{dyn})$
$R_p = 1259.615 \, (\text{dyn} \cdot \text{s}/\text{cm}^5)$  $C = 2.335 \times 10^{-4} \, (\text{cm}^5/\text{dyn})$
$L = 8.266 \, (\text{dyn} \cdot \text{s}^2/\text{cm}^5)$  $SV = 75.8 \, (\text{cc}/\text{beat})$
$W_s = 70.2 \, (\text{J}/\text{min})$ SOLID LINE: PRESSURE WAVEFORM AT THE RADIUS ARTERY
 (62.3/119.9mmHg)
DASHED LINE: PRESSURE WAVEFORM AT THE AORTA
 (64.0/105.0mmHg)

SOLID LINE: PRESSURE WAVEFORM AT THE RADIUS ARTERY
(76.7/118.9mmHg)
DASHED LINE: PRESSURE WAVEFORM AT THE AORTA
(95.9/145.0mmHg)

DEVICE FOR MEASURING PHYSIOLOGICAL STATE

This application is a continuation of Ser. No. 08/860,579 filed Jul. 24, 1997, which is a 371 of PCT/JP96/03211 filed Nov. 1, 1996, the entire contents of which are incorporated herein by reference.

BACKGROUND OF THE INVENTION

1. Field of the Invention

The present invention relates to an optimal device for measuring physiological state which is used to measure conditions in the human body. More specifically, the present invention relates to a device for analyzing pulse waves used to diagnose the circulatory system in the human body, and to a sphygmomanometer which evaluates compliance and resistance in the blood vessels at the center and periphery of the circulatory system based on the physiological state measured at the periphery of the human body, and estimates blood pressure at the center of the circulatory system.

2. Background Art

Blood pressure and heart rate are most commonly used when diagnosing the condition of the circulatory system in the human body. However, in order to carry out a more detailed diagnosis, it becomes necessary to measure the so-called circulatory state parameters of compliance and viscous resistance in the blood vessels. Moreover, in the case where these parameters are expressed using a model, a lumped four parameter model may be employed as a model for expressing the behavior of the arterial system.

The pressure waveform and blood flow volume at the proximal portion of the aorta and at the site of insertion of a catheter into an artery need to be measured in order to measure these circulatory state parameters, however. For this purpose, a direct method of measurement, in which a catheter is inserted into an artery, or an indirect method employing supersonic waves or the like, may be applied. However, the former method is invasive, and employs a large device, while the latter method, although permitting non-invasive observation of blood flow within the blood vessels, requires training and, moreover, necessitates a large device to carry out the measurements.

Accordingly, the present inventors discovered a method for approximating the parameters in a lumped four parameter model by measuring just the pulse waveform at the radius artery and the stroke volume. Thereafter, the present inventors proposed a pulsewave analysis device capable of carrying out an evaluation of the circulatory state parameters in an easy and non-invasive method by employing this method (see Japanese Patent Laid-open Publication No. Hei 6-205747, Title: Device for Analyzing Pulsewaves).

However, the aforementioned method does not employ a model which treats blood vessel compliance at the periphery and center of the arterial system separately. Accordingly, when exercising, or in cases where a pharmacological agent effecting circulatory state has been administered to a patient, it is not possible to evaluate the separate effects of that medication at the periphery and center of the arterial system.

A brief explanation will now be made of the aforementioned measurement of blood pressure.

In the non-invasive sphygmomanometer conventionally employed, a cuff is attached to the upper arm, for example, of a test subject, pressure is applied to the cuff and the pulsewave of the test subject is detected to provide a measurement of blood pressure. Japanese Patent Application Laid Open No. Hei 4-276234, for example, discloses a sphygmomanometer at the periphery of a test subject's body. Namely, as shown in FIG. 29, cuff 110 is wrapped around the upper arm of a test subject, and a band 138 is wrapped around the subject's wrist 140. Pulsewave sensor 134 is attached to the radius artery of the test subject, and the test subject's pulsewave is detected. After applying pressure to cuff 110, the conventional oscillometric method is employed to measure the systolic and diastolic pressure values as the pressure falls.

However, if blood pressure values at the periphery and center of the arterial system in the human body are actually measured, a difference in center and peripheral blood pressure values is observed, particularly in the case of the systolic pressure value. Moreover, the degree of this difference varies depending on the shape of the pulsewave which is observed at the periphery of the arterial system. FIGS. 22 through 24 are provided to explain this variation in blood pressure values according to pulsewave shape. The pressure waveform and systolic/diastolic pressure values at the aorta, which is at the center of the arterial system, and the pressure waveform and systolic/diastolic pressure values at the radius artery, which is at the periphery of the arterial system, are shown in these figures.

FIG. 22 shows the first type of pulse waveform, wherein the systolic pressure value obtained at the aorta is indicated by the dashed line and the systolic pressure value obtained from the radius artery is indicated by the solid line. Although the systolic pressure value obtained at the radius artery is slightly higher, these blood pressure values may be viewed as almost equivalent. In the case of the second type of pulse waveform shown in FIG. 23, however, the difference between the systolic pressure values obtained at the aorta and at the radius artery is 14.9 mmHg, a considerably greater difference than observed in the case of the Type I pulse waveform shown in FIG. 22. Further, in the case of the third type of pulse waveform shown in FIG. 24, the difference between the systolic pressure values is even greater, at 26.1 mmHg. Moreover, in contrast to the Type I and Type II pulse waveforms, in the case of a Type III pulse waveform, the pressure waveform obtained at the aorta is higher in its entirety than that of the pressure waveform obtained at the radius artery. Thus, based on these figures, the diastolic pressure value at the radius artery does not depend on the shape of the pulsewave, but is approximately the same for each pulsewave type.

A brief explanation will now be made of the Type I, Type II and Type III pulsewaves described above. A Type I pulse waveform is observed in a person of normal health. The waveform is relaxed and loose, and is characterized by a fixed rhythm with little disruption. On the other hand, a Type II pulse waveform demonstrates a sharp rise followed immediately by a fall. The aortic notch is deep, while the subsequent peaks in the expansion phase are significantly higher than usual. A Type III pulse waveform rises sharply, with blood pressure remaining elevated for a fixed period of time thereafter, rather than immediately falling off.

As may be gathered from these figures, it is possible for the peripheral blood pressure value obtained at the radius artery or upper arm to be elevated, while the blood pressure value obtained at the proximal portion of the aorta, i.e., at the center of the arterial system, is low. Further, the opposite situation is also possible, namely, the blood pressure value at the periphery is low, while the blood pressure value at the center of the arterial system is high. This relationship will differ depending on the shape of the pulse waveform, and, moreover, is realistically expressed in the shape of the pulse waveform.

For example, when a hypertensive agent is administered to a patient as a treatment for high blood pressure, the drug's effect is observed based on the blood pressure at the radius artery. In this case, however, it is possible that the blood pressure at the center of the arterial system is not actually reduced, even if there is a drop in the blood pressure value measured at the periphery. Accordingly, it can be difficult to correctly ascertain the drug's effect based only on the peripheral blood pressure value. Conversely, even if no change is observed in the blood pressure at the periphery of the arterial system, the actual load on the heart may in fact have been reduced if there is a change in the pressure waveform at the aorta, and the blood pressure at the center of the arterial system drops. In this case, the drug's effect has been fully expressed, even though there was no reduction in blood pressure at the periphery of the arterial system. Accordingly, it is difficult to determine this fact based only on the blood pressure at the periphery of the arterial system.

Accordingly, when measuring blood pressure, the correct approach is to observe the extent of the actual load on the heart. This is because when a determination is made based on blood pressure values measured at the periphery of the arterial system, as has been the conventional practice, there is a chance that the load on the heart will be over or under evaluated.

DISCLOSURE OF THE INVENTION

The present invention was conceived in consideration of the above circumstances, and has as its first objective the provision of a device capable of evaluating circulatory state parameters in a non-invasive method, and more particularly, to the provision of a device for analyzing pulse waves that is capable of evaluating compliance and resistance in blood vessels at the center and periphery of the arterial system separately.

Further, the present invention's second objective in the provision of a sphygmomanometer capable of obtaining the blood pressure value at the center of the arterial system from pulse waveforms measured at the periphery of the arterial system.

The first standpoint of the present invention is characterized in the provision of a measuring means for measuring physiological state, and an analyzing means for calculating circulatory state parameters, including the viscoelasticity of the aorta, as circulatory state parameters which show the circulatory state of an organism's arterial system from the center to the periphery thereof, based on the physiological state of the organism.

Thus, since circulatory state parameters, including viscoelasticity at the aorta, in the arterial system of an organism are calculated, it is possible to achieve a more precise evaluation since the circulatory state of the arterial system, which extends from the center to the periphery of the organism's body, is separated into a center component and a periphery component.

In one embodiment of the present invention, circulatory state parameters are determined by approximating the aforementioned circulatory state parameters in the organism's arterial system with an electric circuit based on a lumped five parameter model. As a result, it is possible to more easily calculate the circulatory state parameters conforming to conditions in the human body, as compared to a lumped four parameter model.

In another embodiment of the present invention, the pulse wave at the periphery of the arterial system is employed as the physiological state, the pressure waveform at the left cardiac ventricle in the body is provided to a lumped five parameter model, and each of the elements making up the lumped five parameter model is determined so as to obtain the pulse waveform at that time. As a result, it is possible to determine circulatory state parameters which closely match the pulsewave at the periphery which was actually measured from the body.

In another embodiment of the present invention, an electric signal corresponding to the pressure in the left cardiac ventricle is approximated by a sinusoidal wave. Thus, it is possible to determine circulatory state parameters which even more accurately express current conditions at the center the arterial system in the body.

The second standpoint of the present invention is characterized in provision of a measuring means for measuring physiological state at the periphery of the arterial system, and a blood pressure calculating means for determining circulatory state parameters showing the circulatory state in the arterial system based on physiological state, and calculating the pressure waveform at the aorta based on the aforementioned circulatory state parameters.

Since the present invention calculates the pressure waveform at the aorta from the physiological state at the periphery of the arterial system in this way, the blood pressure value at the aorta can be estimated using just conditions at the periphery of the arterial system. As a result, there is no concern that a false conclusion will be reached, such as deciding that an administered pharmacological agent had no effect because no change was observed in blood pressure measured at the periphery. Thus, it becomes possible tow correctly ascertain the effect of an administered pharmacological agent, making the present invention extremely useful when selecting drugs such as hypertensive agents and the like.

Further, since one embodiment of the present invention provides that parameters including viscoelasticity at the aorta are selected as circulatory state parameters, it is possible to make an evaluation of the circulatory state at the center and at the periphery of the arterial system separately. As a result, an even more accurate estimation of blood pressure is possible.

Moreover, another embodiment of the present invention provides that circulatory state parameters are determined by approximating the circulatory state of the arterial system using an electric circuit based on a lumped five parameter model. Therefore, it is possible to obtain the blood pressure value at the aorta which more closely conforms with conditions in the human body.

Another embodiment of the present invention employs the pulsewave at the periphery of the arterial system as the physiological state, provides the pressure waveform at the left cardiac ventricle to a lumped five parameter model, and determines each element making up the model so as to obtain the pulsewave at this time. As a result, it is possible to determine blood pressure at the aorta using circulatory state parameters which closely match the pulsewave at the periphery which is actually measured in the body.

In another embodiment of the present invention, blood pressure at the aorta is estimated by determining circulatory state parameters without detecting stroke volume. Thus, blood pressure measurements can be made without causing the test subject any unpleasant discomfort or inconvenience.

In another embodiment of the present invention, the values of the circulatory state parameters are adjusted so that the calculated value of stroke volume which is obtained from the pressure waveform of the aorta is equal to the actual measure value of the stroke volume which is obtained from the body. Thus, it is possible to even more precisely estimate blood pressure at the aorta.

In another embodiment of the present invention, the workload on the heart is calculated based on the pressure waveform at the aorta. Thus, even when no notable change is observed in the blood pressure value obtained at the periphery of the arterial system, it is possible to quantitatively indicate the actual load on the heart. Accordingly, it is possible to carry out an even more exact evaluation of a treatment method employing a hypertensive agent, for example.

PREFERRED EMBODIMENTS OF THE PRESENT INVENTION

<First Embodiment>

A first embodiment of the present invention will now be explained with reference to the accompanying figures.

Figure 1:
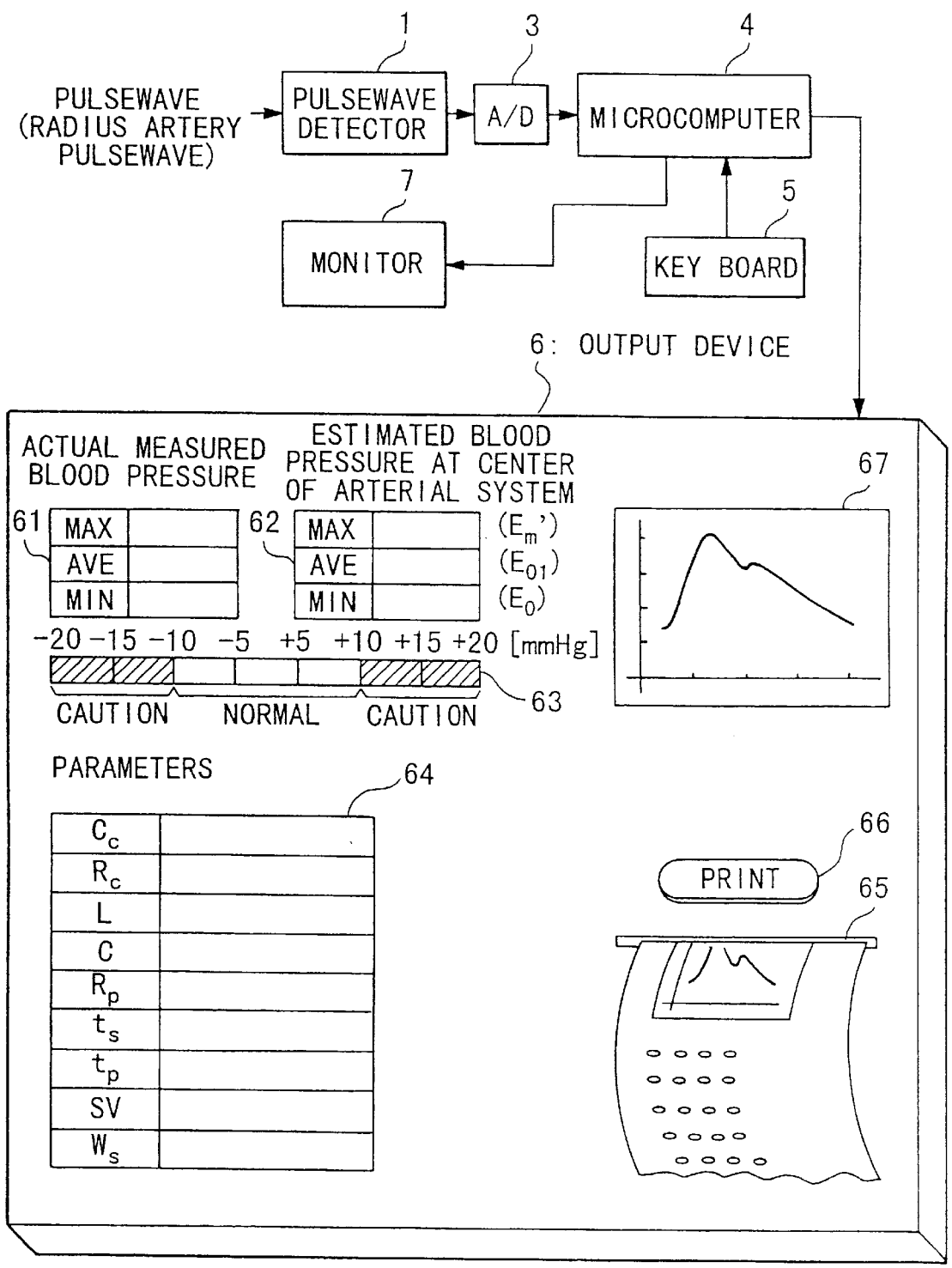
FIG. 1 is a block diagram showing the structure of a pulsewave analysis device according to one embodiment of the present invention.

FIG. 1 is a block diagram showing the composition of the sphygmomanometer employed in this embodiment. In this embodiment, circulatory state parameters for the arterial system in the human body are evaluated based on information obtained from the body using non-invasive sensors. The specific details of these circulatory state parameters will be explained later.

Figure 2:
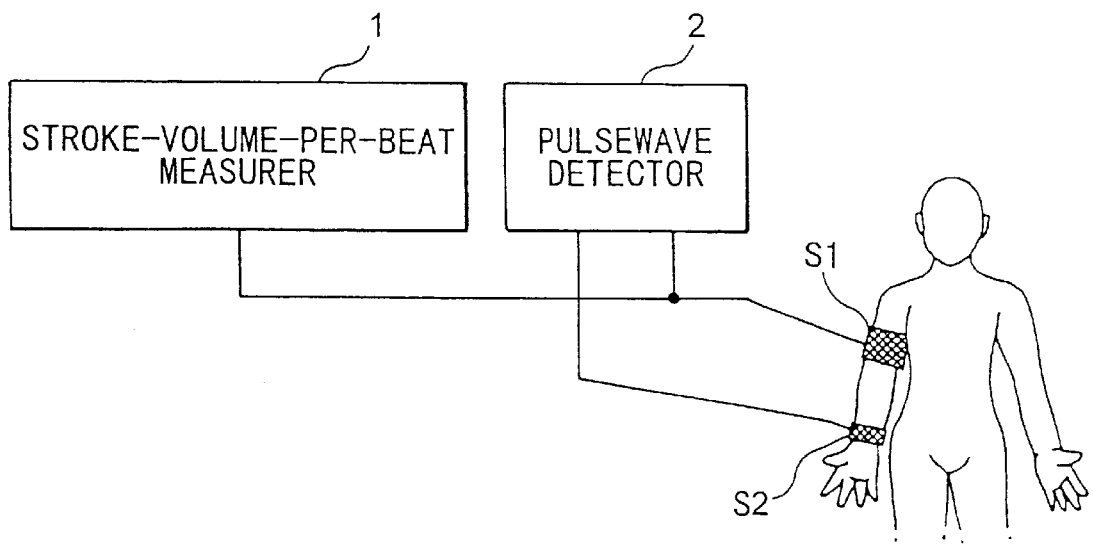
FIG. 2 is a diagram showing the conditions under which measurements employing a pulsewave detector 1 and a stroke-volume measurer 2 were conducted in this embodiment.

In FIG. 1, a pulsewave detector 1 detects the pulsewave at the radius artery via a pressure sensor S2 which is attached to the wrist of a test subject as shown in FIG. 2. Additionally, pulsewave detector 1 detects the blood pressure of the test subject via a cuff S1 attached to the upper arm of the subject as shown in FIG. 2. Pulsewave detector 1 corrects the measured radius artery pulsewave for blood pressure, and outputs the result as an analog electric signal. The analog signals are input to an A/D (analog/digital) converter 3, and are converted to digital signals at a given sampling period.

Stroke-volume measurer 2 is connected to cuff S1 as shown in FIG. 2, and measures the stroke volume, i.e., the amount of blood which flows out from the heart per beat, via cuff S1. The results of this measurement are output in the form of a digital signal as stroke-volume data. A device which carries out measurements using a contraction phase area method may be employed for this type of stroke-volume measurer 2.

Microcomputer 4 houses a waveform memory for storing the pulse waveforms which are taken up from the A/D converter 3, and houses a temporary recording memory which is employed as an operational region. Microcomputer 4 carries out the various processing noted below in accordance with commands which are input from keyboard 5, which is an input device, and outputs the results obtained from processing to output device 6. The processing steps which follow will be explained in greater detail under the explanation of the present invention's operation which follows later.

1. Pulsewave readout processing, in which time series digital signals of the radius artery waveform obtained via A/D converter 3 are taken up in the waveform memory (omitted from figures) which housed in microcomputer 4.
2. Averaging processing, in which the radius artery waveform taken up in waveform memory is averaged at each beat, and a radius artery waveform (hereinafter, referred to as "averaged waveform") corresponding to one beat is obtained.
3. Uptake processing, in which stroke-volume data is taken up in the temporary recording memory inside microcomputer 4.
4. Parameter calculation processing, in which an equation expressing the radius artery waveform corresponding to one beat is obtained, and each of the parameters in an electric model which corresponds to the arterial system is calculated based on this equation.
5. First output processing, in which the obtained parameters are output to output device 6 as circulatory state parameters.
6. Second output processing, in which the pulse waveform at the proximal portion of the aorta is determined from the obtained parameters, the systolic pressure value, diastolic pressure value, and the heart's workload at the proximal portion of the aorta are calculated, and these results are output to output device 6.

Output device 6 will now be explained in detail with reference to FIG. 1. In this figure, the numeral 61 indicates a measured blood pressure display, which displays systolic and diastolic pressure values actually measured, and the average blood pressure value. 62 is a display for displaying the estimated blood pressure value at the center of the arterial system. Display 62 displays average blood pressure $E_{0I}$, systolic pressure $E_m'$, and diastolic pressure $E_0$ at the center of the arterial system which are obtained as a result of processing which will be described below. 63 is an alarm display which is composed of a plurality of LEDs which are disposed in a horizontal row. These LEDs light up in response to a difference between the systolic pressure $E_m'$ at the center of the arterial system and the a systolic pressure value actually measured. Namely, when the difference between the former and the latter is less than ±10 mmHg, then a green LED stating "NORMAL" is illuminated. Conversely, when the difference between the former and the latter exceeds ±10 mmHg, then a red LED stating "CAUTION" is illuminated.

64 is a parameter display. When capacitance $C_c$, electrical resistance $R_c$, inductance L, capacitance C, electrical resistance $R_p$, time duration t, of rising pressure in the left cardiac ventricle, time duration $t_p$ of a single beat, stroke volume SV, and workload $W_s$ are supplied from microcomputer 4, parameter display 64 displays these parameters. These parameters will be explained in detail below. 67 is a CRT display for displaying a variety of waveforms, such as the waveform at the radius artery, the pressure waveform at the left cardiac ventricle, the pressure waveform of the aorta, and the like. 65 is a printer which prints out on paper the waveforms displayed on CRT display 67 and the various data displayed on measured blood pressure display 61, estimated central blood pressure display 62, warning display 63, and parameter display 64, when print command button 66 is depressed.

The significance of a warning display on warning display 63 will now be explained.

Figure 22:
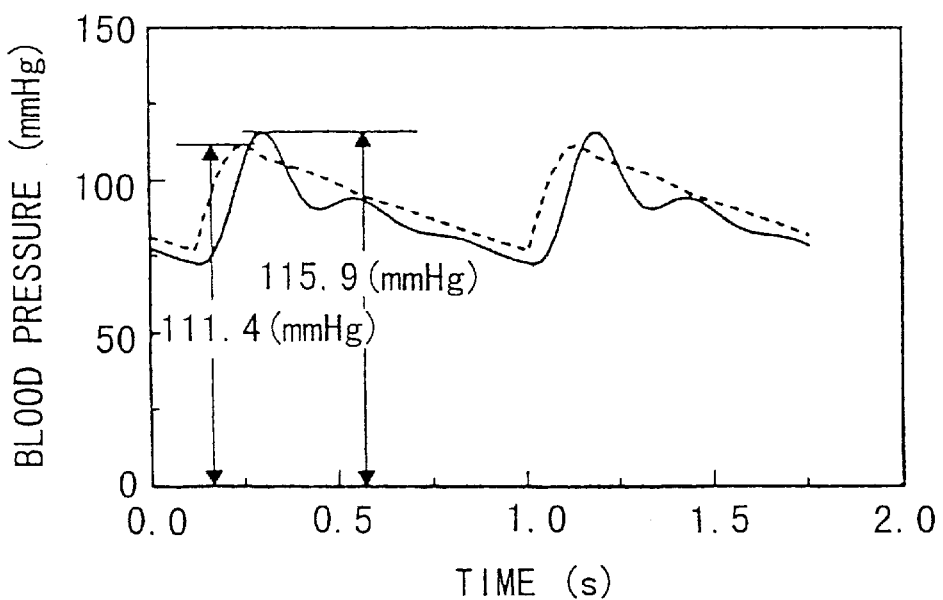
FIG. 22 is a diagram showing the relationship between the pressure waveform at the aorta (dashed line) and the radius artery waveform (solid line) in a Type I pulsewave.
Figure 23:
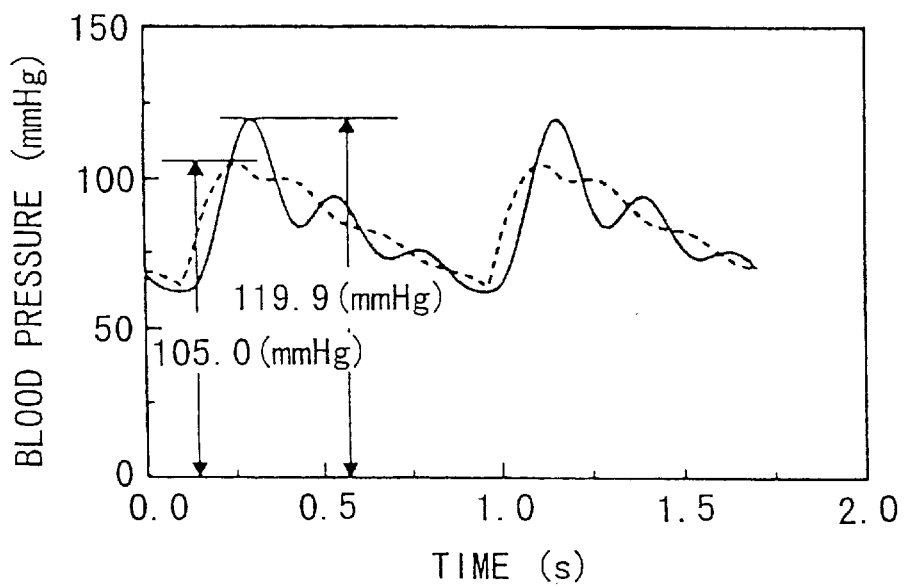
FIG. 23 is a diagram showing the relationship between the pressure waveform at the aorta (dashed line) and the radius artery waveform (solid line) in a Type II pulsewave.
Figure 24:
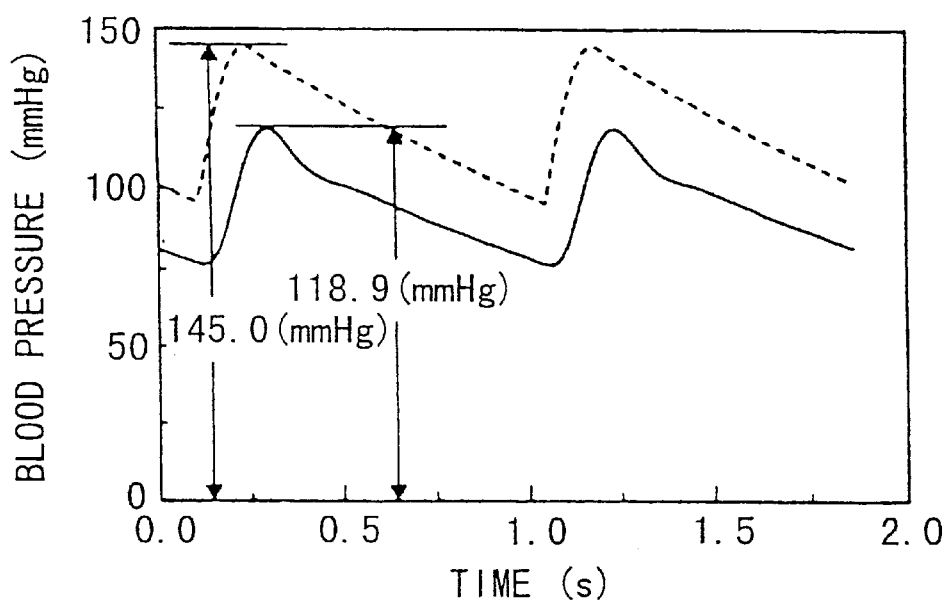
FIG. 24 is a diagram showing the relationship between the pressure waveform at the aorta (dashed line) and the radius artery waveform (solid line) in a Type III pulsewave.
Figure 25:
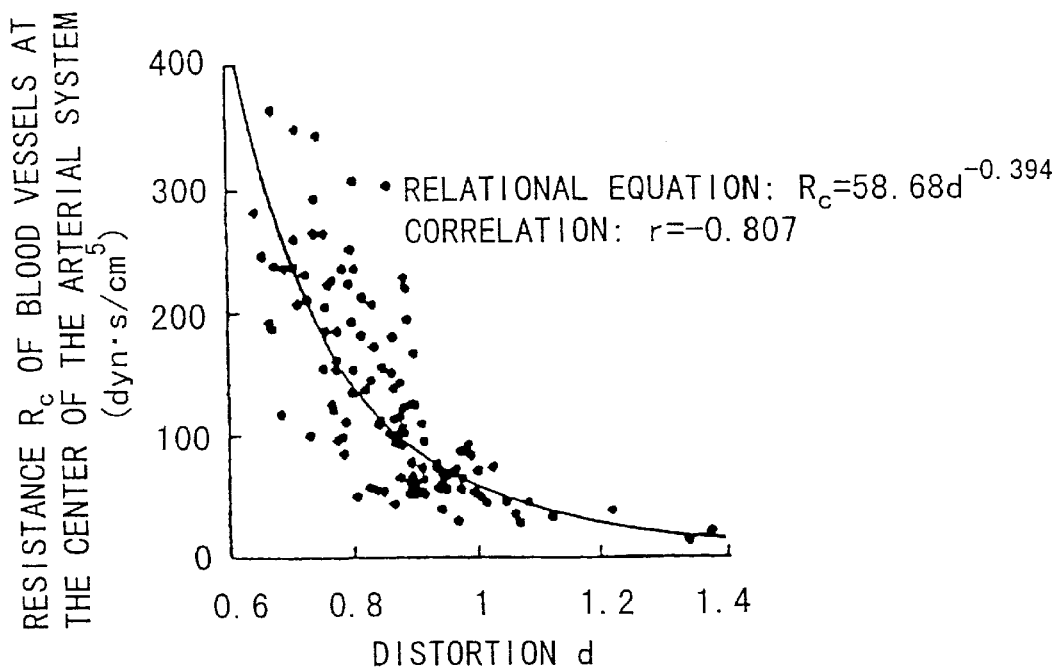
FIG. 25 is a diagram showing the relationship between resistance $R_c$ in blood vessels at the center of the arterial system and distortion d.
Figure 26:
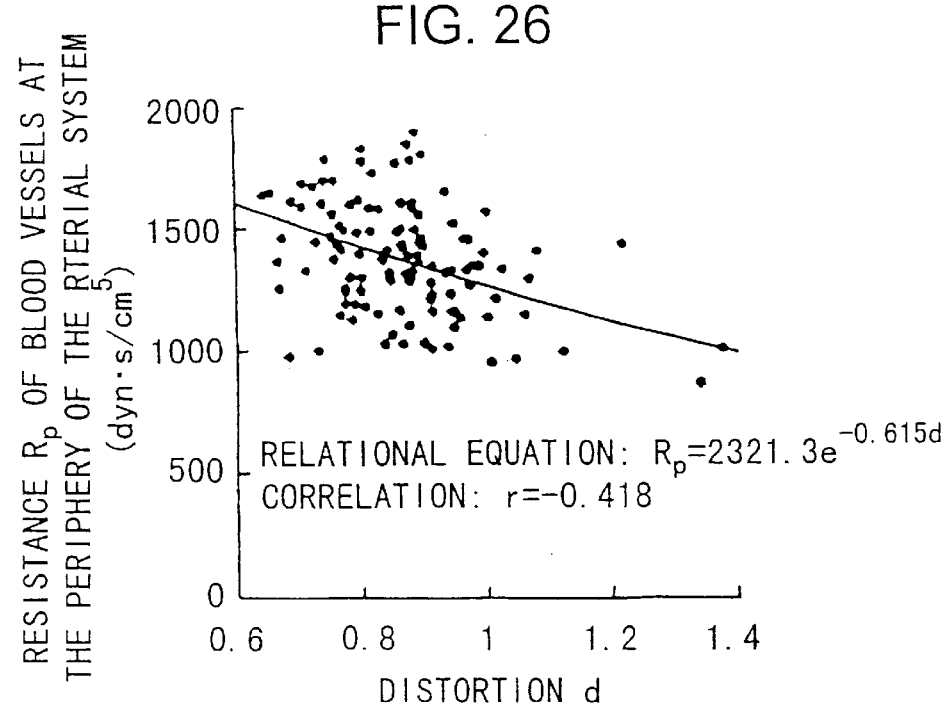
FIG. 26 is a diagram showing the relationship between resistance $R_p$ in blood vessels at the periphery of the arterial system and distortion d.
Figure 27:
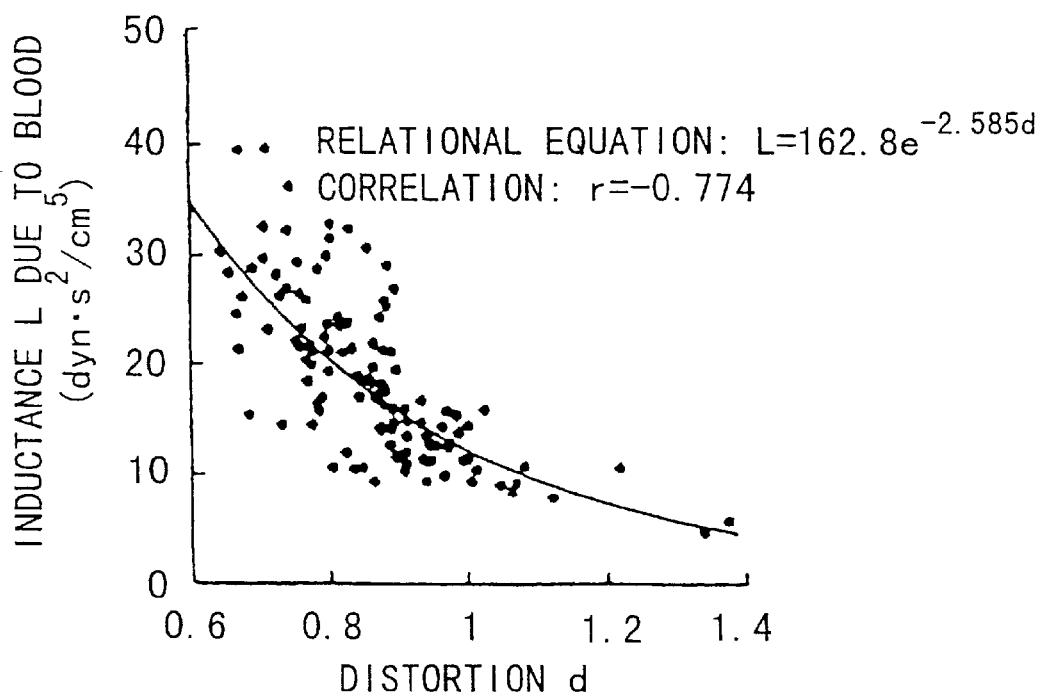
FIG. 27 is a diagram showing the relationship between inertia L from blood flow and distortion d.
Figure 28:
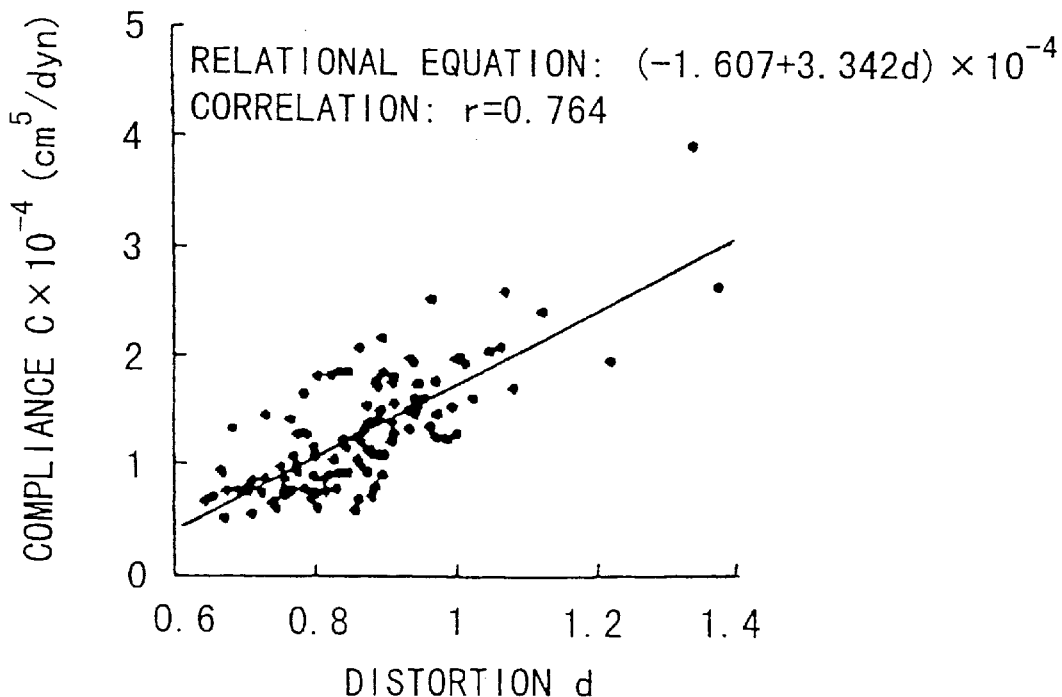
FIG. 28 is a diagram showing the relationship between compliance C and distortion d.

As explained for FIGS. 22 through 24 previously, there are three types of differences which may be noted between the systolic pressure values of the estimated pressure waveform of the aorta and the radius artery waveform. When the pulse waveform is a Type I variety (FIG. 22), then it is very likely that the test subject is a healthy individual. On the other hand, test subjects demonstrating Type II or Type III pulse waveforms are frequently in poor health.

For example, the Type II waveform (FIG. 23) is caused by an anomaly the state of blood flow, and is highly likely in patients suffering from a mammary tumor, liver or kidney ailments, respiratory ailments, stomach or intestinal ailments, inflammation, or the like. The Type III waveform, on the other hand, is caused by an increase in tension in the blood vessel walls, and is very likely in patients having liver or gall ailments, dermatological ailments, high blood pressure, or pain ailments.

Accordingly, the present embodiment provides that a warning display be carried out by means of illuminating a red LED when there is believed to be an anomaly in the difference between systolic pressure values as described above.

In the preceding example, a diagnosis was made based on the difference between the systolic pressure of the pressure waveform at the aorta and the systolic pressure value of the waveform of the radius artery. However, it is also acceptable to employ the difference in minimum or average blood pressure values, instead of the difference in systolic pressure values. Moreover, it is of course acceptable to carry out diagnosis using the differences in maximum, minimum and average blood pressure values together.

The present embodiment newly employs a "lumped five parameter model" as an electrical model for the arterial system. There are various components which determine the behavior of the circulatory system in the human body. From among these, the component of aortic compliance has been added to the four parameters of inertia due to blood at the center of the arterial system, resistance (viscous resistance) in blood vessels at the center of the arterial system due to blood viscosity, compliance (viscoelasticity) of blood vessels at the periphery of the arterial system, and resistance (viscous resistance) in blood vessels at the periphery of the arterial system, which were employed in the lumped four parameter model disclosed in Japanese Patent Application Hei 6-205747 (Title: Device for Analyzing Pulsewaves), to comprise this lumped five parameter model. An electric circuit has been employed to model these parameters. Additionally, we note here that compliance is a quantity expressing the degree of pliability of the blood vessels.

Figure 3A:
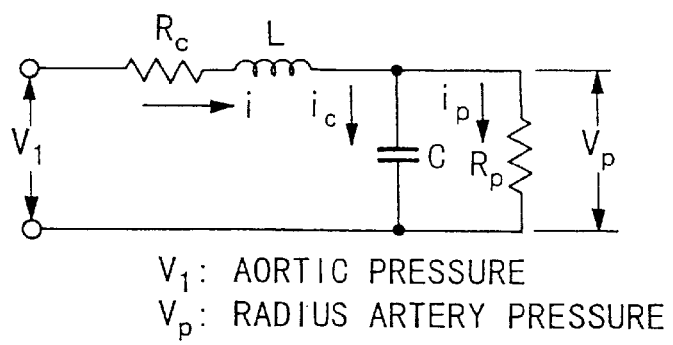
FIG. 3(a) is a circuit diagram showing a lumped four parameter model which models the arterial system in the human body.
Figure 3B:
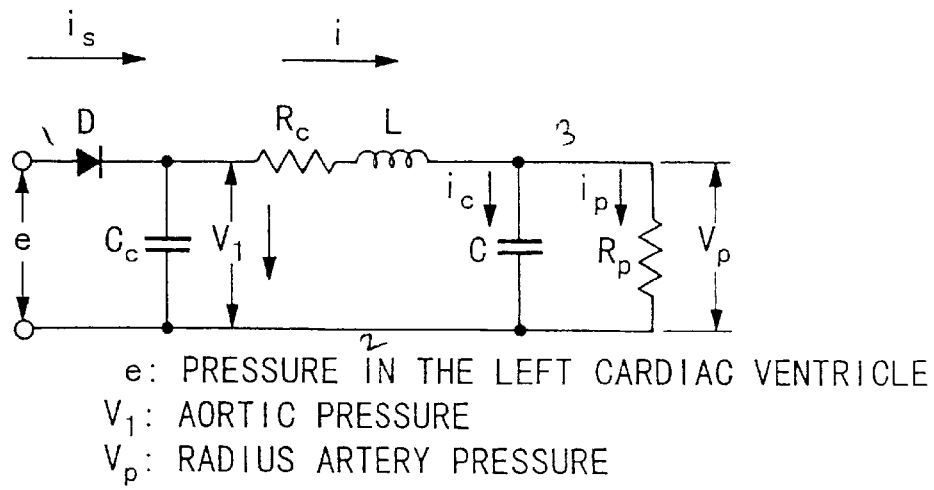
FIG. 3(b) is a circuit diagram showing a lumped five parameter model which models the arterial system in the human body.

FIG. 3(a) shows a circuit diagram for a lumped four parameter model, while FIG. 3(b) shows a circuit diagram for a lumped five parameter model. The relationship between the parameters and the elements making up the lumped five parameter model is as follows.

Capacitance $C_c$: aortic compliance (cm$^5$/dyn)

Electrical resistance $R_c$: blood vessel resistance due to blood viscosity at the center of the arterial system (dyn·s/cm$^5$)

Inductance L: inertia of blood at center of arterial system (dyn·s$^2$/cm$^5$)

Capacitance C: compliance of blood vessels at periphery of arterial system (cm$^5$/dyn)

Electrical resistance $R_p$: blood vessel resistance at periphery of arterial system due to blood viscosity (dyn·s/cm$^5$)

Currents i, $i_p$, $i_c$, and $i_s$, which are flowing through each part of the electrical circuit, correspond to blood flow (cm$^3$/s). Current i is the blood flow at the aorta and current $i_s$ is the blood flow pumped out from the left cardiac ventricle. Input voltage e corresponds to the pressure in the left cardiac ventricle (dyn/cm$^2$), while voltage $v_l$ corresponds to the pressure (dyn/cm$^2$) of the proximal portion of the aorta. Terminal voltage $v_p$ of capacitance C corresponds to the pressure (dyn/cm$^2$) at the radius artery. Further, diode D shown in FIG. 3(b) corresponds to the aortic valve. Diode D is on (valve open) during a period corresponding to contraction, and off (valve closed) during a period corresponding to expansion.

As will be explained below, these five parameters are not calculated all at once in the present embodiment. Rather, the lumped four parameter model disclosed in the reference cited above is employed to calculate all parameters with the exception of capacitance $C_c$, after which capacitance $C_c$ is determined. A theoretical explanation of the behavior of the lumped four parameter model shown in FIG. 3(a) will now be made.

The following differential equation is established for the lumped four parameter model shown in FIG. 3(a).

$$v_1 = R_c i + L \frac{di}{dt} + v_p \qquad (1)$$

Current i in the above equation may be expressed as:

$$i = i_c + i_p = C \frac{dv_p}{dt} + \frac{v_p}{R_p} \qquad (2)$$

Thus, equation (1) may be rewritten as follows:

$$v_1 = LC \frac{d^2 v_p}{dt^2} + \left(R_c C + \frac{L}{R_p}\right)\frac{dv_p}{dt} + \left(1 + \frac{R_c}{R_p}\right)v_p \qquad (3)$$

As is conventionally known, the general solution for a second order constant coefficient ordinary differential equation may be obtained by summing the particular solution (steady-state solution) which satisfies equation (3) and the transient solution which satisfies the following differential equation.

$$0 = LC \frac{d^2 v_p}{dt^2} + \left(R_c C + \frac{L}{R_p}\right)\frac{dv_p}{dt} + \left(1 + \frac{R_c}{R_p}\right)v_p \qquad (4)$$

The solution for differential equation (4) is obtained as follows. First, the damped oscillating waveform expressed by the following equation is assumed as the solution for differential equation (4).

$$v_p = \exp(st) \qquad (5)$$

Substituting equation (5) into equation (4), equation (4) may be rewritten as follows.

$$\left\{LCs^2 + \left(R_c C + \frac{L}{R_p}\right)s + \left(1 + \frac{R_c}{R_p}\right)\right\}v_p = 0 \qquad (6)$$

Solving equation (6) for s yields:

$$s = \frac{-\left(R_c C + \frac{L}{R_p}\right) \pm \sqrt{\left(R_c C + \frac{L}{R_p}\right)^2 - 4LC\left(1 + \frac{R_c}{R_p}\right)}}{2LC} \qquad (7)$$

In equation (7), when $$\left(R_c C + \frac{L}{R_p}\right)^2 < 4LC\left(1 + \frac{R_c}{R_p}\right) \qquad (8)$$

then the radicand of the radical sign in the second term becomes negative, and s is as follows.

$$s = \frac{-\left(R_c C + \frac{L}{R_p}\right) \pm j\sqrt{4LC\left(1 + \frac{R_c}{R_p}\right) - \left(R_c C + \frac{L}{R_p}\right)^2}}{2LC} \qquad (9)$$

$$= -\alpha \pm j\omega$$

Where, $\alpha$ is the damping factor and $\omega$ is the angular frequency.

$$\alpha = \frac{R_c C + \frac{L}{R_p}}{2LC} \qquad (10)$$

$$= \frac{L + R_p R_c C}{2LCR_p}$$

$$\omega = \frac{\sqrt{4LC\left(1 + \frac{R_c}{R_p}\right) - \left(R_c C + \frac{L}{R_p}\right)^2}}{2LC} \qquad (11)$$

Further, when $$A_1 = LC \qquad (12)$$

$$A_2 = \frac{L + R_c R_p C}{R_p} \qquad (13)$$

$$A_3 = \frac{R_C + R_p}{R_p} \qquad (14)$$

then equations (10) and (11) above may be expressed as follows:

$$\alpha = \frac{A_2}{2A_1} \qquad (15)$$

$$\omega = \sqrt{\frac{A_3}{A_1} - \alpha^2} \qquad (16)$$

By confirming the value of s in this way, a solution may be obtained which satisfies differential equation (4). Based on the preceding view, then, equation (5) may be employed as an equation approximating the damped oscillating component which is included in the response waveform of a the lumped four parameter model.

Next, the pressure waveform at the proximal portion of the aorta will be modeled. In general, the pressure waveform at the proximal portion of the aorta demonstrates a shape as indicated by the heavy line in FIG. 4. In this figure, $t_p$ is the time duration of a one beat in a waveform, while $t_s$ is the time period during which pressure increases in the left cardiac ventricle. In a lumped four parameter model, this pressure waveform is approximated by the triangular wave shown in FIG. 5. When the amplitude and duration of the approximated waveform are indicated as $E_o$, $E_m$, $t_p$, and $t_{p1}$, then the aortic pressure $v_I$ at an optional time t may be expressed by the following equation. Here, $E_o$ is the diastolic pressure (blood pressure during expansion phase), $E_m$ is the pulse pressure, ($E_o + E_m$) is the systolic pressure (blood pressure during contraction phase), to is the time duration of one beat, and $t_{p1}$ is the time duration from the rise in aortic pressure until blood pressure falls to a minimum value. In the interval $0 \leq t < t_{p1}$:

$$v_1 = E_o + E_m\left(1 - \frac{t}{t_{p1}}\right) \tag{17}$$

In the interval $t_{p1} \leq t < t_p$:

$$v_I = E_o \tag{18}$$

The response waveform $v_p$ (ie., radius artery waveform) when voltage $v_I$ which is expressed using equations (17) and (18) is input into the equivalent circuit shown in FIG. 3(a) is as follows.
In the interval $0 \leq t < t_{p1}$:

$$v_p = E_{\min} + B\left(1 - \frac{t}{t_b}\right) + D_{m1}\exp(-\alpha t)\sin(\omega t + \theta_1) \tag{19}$$

In the interval $t_{p1} < t \leq t_p$:

$$v_p = E_{\min} + D_{m2}\cdot\exp\{-\alpha(t-t_{p1})\}\cdot\sin\{\omega(t-t_{p1}) + \theta_2\} \tag{20}$$

Figure 11:
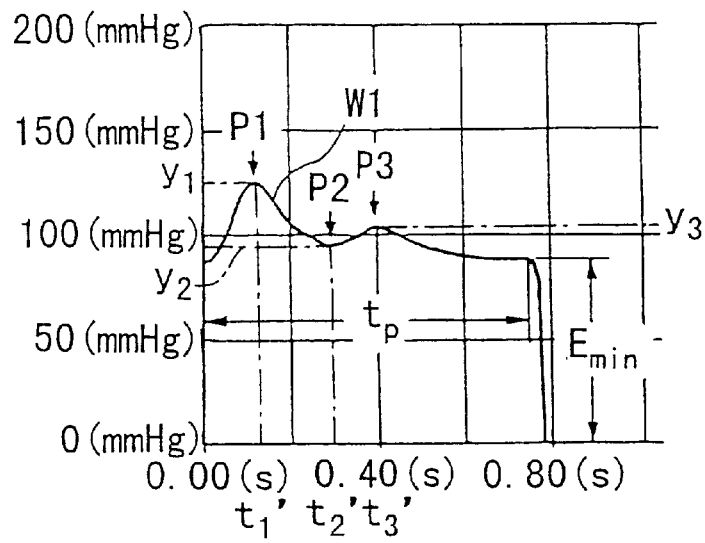
FIG. 11 is a waveform diagram showing an example of the waveform at the radius artery obtained through an averaging process in the pulsewave analysis device.

Here, $E_{\min}$ is the diastolic pressure value in the radius artery waveform which is measured by pulsewave detector 1 (refer to FIG. 11 explained below).

The third term from the right in equation (19) and the second term from the right in equation (20) are the damped oscillating components in equation (5) explained above. $\alpha$ and $\omega$ in these terms may be obtained from equations (15) and (16). B, $t_b$, $D_{m1}$, and $D_{m2}$ are constants which are calculated in accordance with a procedure described below.

Next, an examination will be made of the constants in equations (19) and (20), with the exception of $\alpha$ and $\omega$ which were already confirmed. To begin with, the following equation is obtained when equations (17) and (19) are substituted into differential equation (3).

$$E_o + E_m\left(1 - \frac{t}{t_{p1}}\right) = \left(1 + \frac{R_c}{R_p}\right)(E_{\min} + B) - \frac{B}{t_b}\left(R_cC + \frac{L}{R_p}\right)t + \tag{21}$$
$$\left\{LC(\alpha^2 - \omega^2)D_{m1} - \alpha D_{m1}\left(R_cC + \frac{L}{R_p}\right) + D_{m1}\left(1 + \frac{R_c}{R_p}\right)\right\}\times\exp(-\alpha t)\sin(\omega t + \theta_1) +$$
$$\left\{\omega D_{m1}\left(R_cC + \frac{L}{R_p}\right) - 2LC\alpha\omega D_{m1}\right\}$$

-continued
$$\exp(-\alpha t)\cos(\omega t + \theta_1)$$

The following conditions are necessary in order to establish the preceding equation (21).

$$E_o + E_m = \left(1 + \frac{R_c}{R_p}\right)(E_{\min} + B) \tag{22}$$
$$= E_o + A_3 B - \frac{B}{t_b}A_2$$

$$\frac{E_m}{t_{p1}} = \frac{B}{t_b}\left(1 + \frac{R_c}{R_p}\right) = \frac{A_3 B}{t_b} \tag{23}$$

$$LC(\alpha^2 - \omega^2) - \alpha\left(R_cC + \frac{L}{R_p}\right) + \left(1 + \frac{R_c}{R_p}\right) = 0 \tag{24}$$

$$R_cC + \frac{L}{R_p} = 2LC\alpha \tag{25}$$

Equations (24) and (25) restrict $\alpha$ and $\omega$, however, these equations are satisfied by $\alpha$ and $\omega$ as obtained according to equations (15) and (16) above.

When equations (18) and (20) are substituted into differential equation (3), the following equation is obtained.

$$E_o = \left(1 + \frac{R_c}{R_p}\right)E_{\min} + \{LC(\alpha^2 - \omega^2)D_{m2} - \tag{26}$$
$$\alpha\left(R_cC + \frac{L}{R_p}\right)D_{m2} + \left(1 + \frac{R_c}{R_p}\right)D_{m2}\}\times$$
$$\exp(-\alpha(t - t_{p1}))\sin(\omega(t - t_{p1}) + \theta_2) +$$
$$\left\{\omega\left(R_cC + \frac{L}{R_p}\right)D_{m2} - 2LC\alpha\omega D_{m2}\right\}\times$$
$$\exp(-\alpha(t - t_{p1}))\cos(\omega(t - t_{p1}) + \theta_2)$$

In addition to equations (24) and (25), it is also necessary to set up the following equation in order to establish equation (26).

$$E_o = \left(1 + \frac{R_c}{R_p}\right)E_{\min} = A_3 E_{\min} \tag{27}$$

Next, each of the constants in equations (19) and (20) will be calculated based on conditional equations (22) through (25) and (27) for setting up differential equation (3).

First, the following equation is obtained for $E_{\min}$ from equation (27).

$$E_{\min} = \frac{E_O}{A_3} \tag{28}$$

An equation for B is obtained from equation (23):

$$B = \frac{t_b E_m}{t_{p1} A_3} \tag{29}$$

When equation (29) is substituted into equation (22), and solved for $t_b$, the following equation is obtained:

$$t_b = \frac{t_{pI}A_3 + A_2}{A_3} \quad (30)$$

Next, values are selected for the remaining constants $D_{m1}$, $D_{m2}$, $\theta_1$, and $\theta_2$ so that radius artery waveform $v_p$ remains continuous over $t=0$, $t_{p1}$, $t_p$, i.e. values are selected which satisfy the following conditions a through d.

a. $v_p(t_{p1})$ in equation (19) and $v_p(t_{p1})$ in equation (20) are equivalent
b. $v_p(t_p)$ in equation (20) and $v_p(0)$ in equation (19) are equivalent
c. The differential coefficients at $t=t_{p1}$ in equations (19) and (20) are equivalent
d. The differential coefficient of equation (19) at $t=0$ and the differential coefficient of equation (20) at $t=t_p$ are equivalent In other words, values are selected for $D_{m1}$ and $\theta_1$ so that:

$$D_{m1} = \frac{\sqrt{D_{11}^2 + D_{12}^2}}{\omega} \quad (31)$$

$$\theta_1 = \tan^{-1}\frac{D_{11}}{D_{12}} \quad (32)$$

where, $$D_{11} = (v_{o1} - B - E_{min})\omega \quad (33)$$

$$D_{12} = (v_{O1} - B - E_{min})\alpha + \frac{B}{t_p} + \frac{i_{OI}}{C} \quad (34)$$

and $v_{o1}$ and $i_{o1}$ are the initial values of $v_p$ and $i_c$ at $t=0$.

Further, values are selected for $D_{m2}$ and $\theta_2$ so that:

$$D_{m2} = \frac{\sqrt{D_{21}^2 + D_{22}^2}}{\omega} \quad (35)$$

$$\theta_2 = \tan^{-1}\frac{D_{21}}{D_{22}} \quad (36)$$

where, $$D_{21} = (v_{o2} - E_{min})\cdot\omega \quad (37)$$

$$D_{22} = (v_{O2} - E_{min})\cdot\alpha + \frac{i_{o2}}{C} \quad (38)$$

and $v_{o2}$ and $i_{o2}$ are the initial values of $v_p$ and $i_c$ at $t=t_{p1}$.

In this manner, then, each of the constants in equations (19) and (20) are obtained.

Next, the following equation for blood vessel resistance $R_c$ is obtained by means of an inverse operation from angular frequency $\omega$ in equation (16).

$$R_C = \frac{L - 2R_p\sqrt{LC(1-\omega^2LC)}}{CR_p} \quad (39)$$

Here, the condition for $R_c$ to be a real and positive number is:

$$\frac{4R_p^2 C}{1+(2\omega R_p C)^2} \leq L \leq \frac{1}{\omega^2 C} \quad (40)$$

In general, $R_p$ and $C$ are on the order of $10^3[\mathrm{dyn\cdot s/cm^5}]$ and $10^{-4}[\mathrm{cm^5/dyn}]$, respectively. $\omega$ may be viewed to be on the order of 10 (rad/s) or greater, since it is the angular frequency of the oscillation component which is superimposed on the pulsewave. For this reason, the lower limit of equation (40) is viewed to be around $1/(\omega^2 C)$. Accordingly, when $L$ is approximated by the following equation (41) for the purposes of simplification $$L = \frac{1}{\omega^2 C} \quad (41)$$

$R_c$ becomes:

$$R_C = \frac{L}{CR_p} \quad (42)$$

From the relationship between equations (41) and (42), the damping constant $\alpha$ in equation (15) becomes:

$$\alpha = \frac{1}{CR_p} \quad (43)$$

Using the relationships between equations (41) through (43), the remaining parameters in the lumped four parameter model may be expressed using $\alpha$, $\omega$, and $L$ as follows.

$$R_p = \frac{\omega^2 L}{\alpha} \quad (45)$$

$$C = \frac{1}{\omega^2 L} \quad (46)$$

Thus, it is clear that the parameters are confirmed by obtaining $\alpha$, $\omega$ and $L$ from the preceding equations (44) through (46).

$\alpha$, $\omega$, $B$ and $t_b$ may be obtained from the actual measured waveform at the radius artery, and $L$ can be calculated based on the stroke volume SV, as will be explained below. The process for calculating $L$ based on stroke volume SV will now be explained.

First, the average value $E_{OI}$ of the pressure wave at the proximal portion of the aorta is obtained from the following equation.

$$E_{01} = \frac{E_o t_p + \frac{t_{pI} E_m}{2}}{t_p} \quad (47)$$

The following equation may be established between $R_c$, $R_p$, $\alpha$, $\omega$, and $L$.

$$R_c + R_p = \alpha L + \frac{\omega^2 L}{\alpha} = (\alpha^2 + \omega^2)\frac{L}{\alpha} \quad (48)$$

The result of dividing the average current i.e., average value $E_{OI}$, flowing through the lumped four parameter model by $(R_c+R_p)$ corresponds to the average value $(SV/t_p)$ of blood flow flowing through the arteries due to the pulse. Accordingly, the following equation may be established.

$$\frac{SV}{t_p} = \frac{\alpha}{(\alpha^2 + \omega^2)L} \frac{1}{t_p}\left(E_o t_p + \frac{t_{pl}E_m}{2}\right) \quad (49)$$

By solving the thus-obtained equation 49 for L, an equation for obtaining L from stroke volume SV may be obtained as follows.

$$L = \alpha \cdot \frac{E_o t_p + \frac{t_{pl}E_m}{2}}{(\alpha^2 + \omega^2)SV} \quad (50)$$

The value corresponding to average current $(1/t_p)\{E_0 t_p + t_{p1}E_m/2)\}$ in equation (49) may be obtained by measuring the blood flow volume, and inductance L may be calculated based on this result. As a device for measuring blood flow volume, there are available devices employing the inductance method, the Doppler method and the like In the case of a device which measures blood rate using the Doppler method, there are available devices employing supersonic waves and laser.

Next, a theoretical explanation will be made of the method for calculating the circulatory state parameters based on a lumped five parameter model. As mentioned before, the circulatory state parameters $R_c$, $R_p$, C, and L are determined using a lumped four, parameter model. Accordingly, the value of capacitance $C_c$ is determined based on these parameters. It is therefore necessary to obtain current i, current $i_s$, voltage $v_1$, and voltage $v_p$ in FIG. 3(b).

Figure 4:
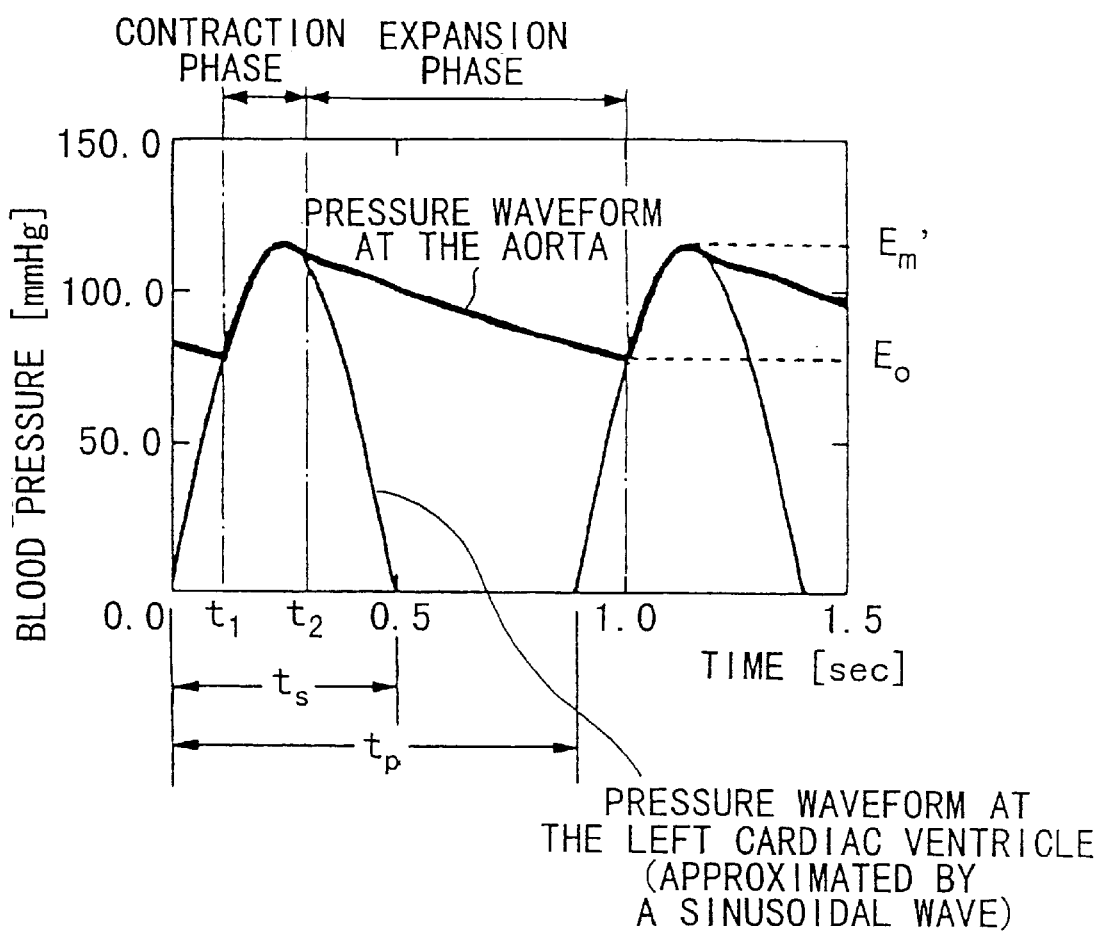
FIG. 4 is a diagram showing the pressure waveform at the left cardiac ventricle and the blood pressure waveform at the proximal portion of the aorta.

First, the pressure waveform at the left cardiac ventricle is approximated with a sinusoidal wave such as shown in FIG. 4. In other words, by setting $\omega_s = \pi/t_s$, the pressure waveform e of the left cardiac ventricle is expressed by the following equation.

$$e = E'_m \sin \omega_s t \quad (51)$$

Figure 5:
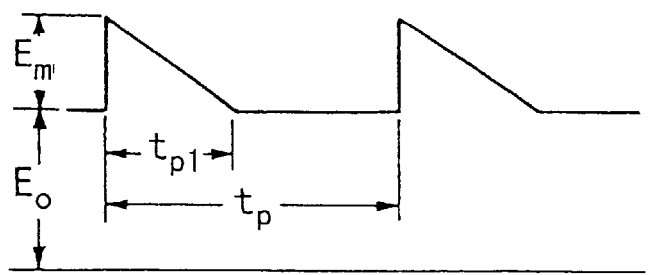
FIG. 5 is a diagram showing a waveform which models the blood pressure waveform at the proximal portion of the aorta.
Figure 6:
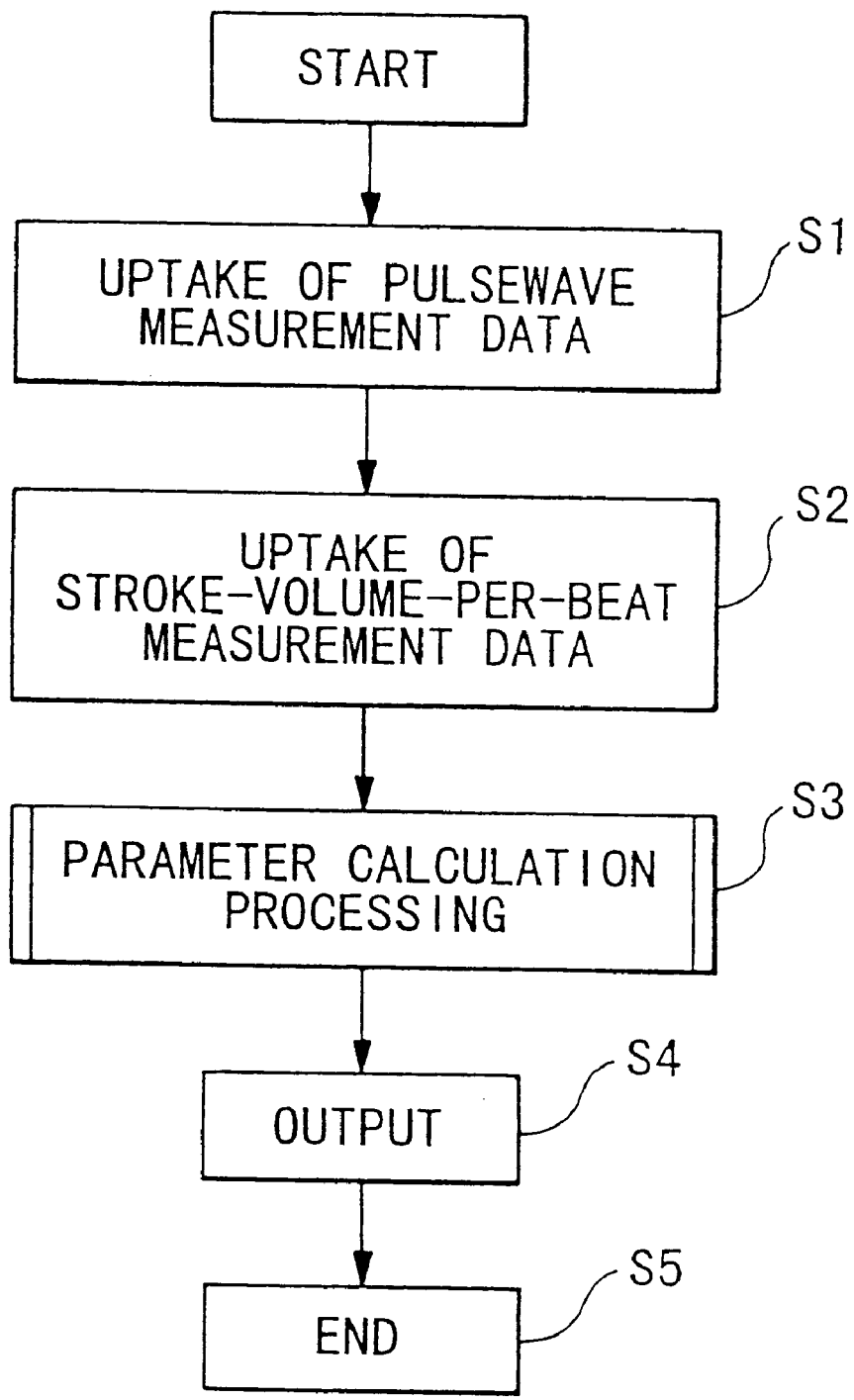
FIG. 6 is a flow chart showing an overview of the operation of the pulsewave analysis device in this embodiment.

Here $E_m'$ is the systolic pressure and, if stated in terms of FIG. 5, corresponds to $(E_m + E_0)$.

An explanation will now be made, taking the cases where time duration t corresponds to the contraction phase of $t_1 \leq t < t_2$ and to the expansion phase $t_2 \leq t < (t_p + t_1)$, as shown in FIG. 4. Here, time $t_1$ and time $t_2$ are the times at which the pressure waveform of the left cardiac ventricle waveform and the pressure waveform of the aorta intersect.

(Contraction Phase)

In this case, the equation $v_1 = e$, as well as equations (1) and (2) for voltage $v_1$ and current i, respectively, are established. Accordingly, the following differential equation is set up from equations (1) through (3), (12) through (14) and (51).

$$A_1 \frac{d^2 v_p}{dt^2} + A_2 \frac{dv_p}{dt} + A_3 v_p = E'_m \sin \omega_s t \quad (52)$$

First, in the same manner as the lumped four parameter model, the steady-state solution $V_{pst}$ for this differential equation is obtained. For this purpose, the following equation is assumed for the steady-state solution $V_{pst}$.

$$v_{pst} = E_1 \cos \omega_s t + E_2 \sin \omega_s t \quad (53)$$

By comparing the coefficients by substituting equation (53) for the term $v_p$ in equation (52), the following two equations are obtained.

$$(A_3 - \omega_s^2 A_1) E_1 + \omega_s A_2 E_2 = 0 \quad (54)$$

$$-\omega_s A_2 E_1 + (A_3 - \omega_s^2 A_1) E_2 = E_{m'} \quad (55)$$

Solving these equations, the following equations (56) and (57) are obtained.

$$E_1 = \frac{-\omega_s A_2 E'_m}{(\omega_s A_2)^2 + (A_3 - \omega_s^2 A_1)^2} \quad (56)$$

$$E_2 = \frac{(A_3 - \omega_s^2 A_1) E'_m}{(\omega_s A_2)^2 + (A_3 - \omega_s^2 A_1)^2} \quad (57)$$

Next, the transient solution $v_{ptr}$ for differential equation (52) is obtained. Setting $v_{ptr} = \exp(\lambda t)$, this is substituted for $v_p$ in the following equation.

$$A_1 \frac{d^2 v_p}{dt^2} + A_2 \frac{dv_p}{dt} + A_3 v_p = 0 \quad (58)$$

As a result, the following equation is obtained.

$$A_1 \lambda^2 + A_2 \lambda + A_3 = 0 \quad (59)$$

Solving this equation for $\lambda$, the following equation is obtained.

$$\lambda = \frac{-A_2 \pm \sqrt{A_2^2 - 4A_1 A_3}}{2A_1} \quad (60)$$

$$= \left(-\frac{A_2}{2A_1}\right) \pm \sqrt{\left(\frac{A_2}{2A_1}\right)^2 - \frac{A_3}{A_1}}$$

Setting $\{A_2/(2A_1)\}^2 < (A_3/A_1)$ (i.e., oscillation mode), the following equation is obtained.

$$\lambda = -\frac{A_2}{2A_1} \pm j\sqrt{\frac{A_3}{A_1} - \left(\frac{A_2}{2A_1}\right)^2} = -\beta_1 \pm j\omega_1 \quad (61)$$

In this case, $$\beta_1 = \frac{A_2}{2A_1} \quad (62)$$

$$\omega_1 = \sqrt{\frac{A_3}{A_1} - \beta_1^2} \quad (63)$$

Here, transient solution $v_{ptr}$ is set as in the following equation.

$$v_{ptr} = (\alpha_1 \cos \omega_1 t + j\alpha_2 \sin \omega_1 t) \exp(-\beta_1 t) \quad (64)$$

As a result, voltage $v_p$ is expressed as the sum of the steady-state solution and the transient solution, and therefore may be obtained from the following equation using equations (53) and (64).

$$v_p = (E_1 \cos \omega_s t + E_2 \sin \omega_s t) + (\alpha_1 \cos \omega_1 t + j\alpha_2 \sin \omega_1 t) \exp(-\beta_1 t) \quad (65)$$

The following equation may be obtained for current i by substituting equation (65) into equation (2).

$$i = \left(\frac{E_1}{R_p} + \omega_s C E_2\right)\cos \omega_s t + \left(-\omega_s C_c E_1 + \frac{E_2}{R_p}\right)\sin \omega_s t + \quad (66)$$

$$\left[\left\{\left(\frac{1-\beta_1 CR_p}{R_p}\right)\cos\omega_1 t - \omega_1 C\sin\omega_1 t\right\}a_1 + \right.$$
$$\left. j\left\{w_1 C\cos\omega_1 t + \left(\frac{1-\beta_1 CR_p}{R_p}\right)\sin\omega_1 t\right\}a_2\right]\exp(-\beta_1 t)$$

Next, the $v_{02}$ and $i_0$ are assumed as the values of $v_p$ and i, respectively, when $t=t_1$ as in the followings equations.

$$i_0 = J_0 + (\alpha_1 J_1 + j\alpha_2 J_2)\exp(-\beta_1 t_1) \tag{67}$$

$$v_{o2} = P_0 + (\alpha_1 P_1 + j\alpha_2 P_2)\exp(-\beta_1 t_1) \tag{68}$$

As a result, equations (65) through (68) may be used to establish the following equations.

$$J_0 = \left(\frac{E_1}{R_p} + \omega_s CE_2\right)\cos\omega_s t_1 + \left(-\omega_s CE_1 + \frac{E_2}{R_p}\right)\sin\omega_s t_1 \tag{69}$$

$$J_1 = \left(\frac{1-\beta_1 CR_p}{R_p}\right)\cos\omega_1 t_1 - \omega_1 C\sin\omega_1 t_1 \tag{70}$$

$$J_2 = \omega_1 C\cos\omega_1 t_1 + \left(\frac{1-\beta_1 CR_p}{R_p}\right)\sin\omega_1 t_1 \tag{71}$$

$$P_0 = E_1\cos\omega_s t_1 + E_2\sin\omega_s t_1 \tag{72}$$

$$P_1 = \cos\omega_1 t_1 \tag{73}$$

$$P_2 = \sin\omega_1 t_1 \tag{74}$$

Next, solving equations (67) and (68) for $\alpha_1$ and $\alpha_2$, the following equations (75) and (76) may be obtained.

$$a_1 = \left\{\frac{(v_{02}-P_0)J_2 - (i_0-J_0)P_2}{J_2 P_1 - J_1 P_2}\right\}\exp(\beta_1 t_1) \tag{75}$$

$$a_2 = \left\{\frac{-(v_{02}-P_0)J_1 + (i_0-J_0)P_1}{j(J_2 P_1 - J_1 P_2)}\right\}\exp(\beta_1 t_1) \tag{76}$$

Next, the relationship expressed by the following equation may be established from equations (70) through (74).

$$J_2 P_1 - J_1 P_2 = \omega_1 C \tag{77}$$

Accordingly, when equations (75) and (76) are substituted into equation (64), and equation (77) is employed, then the following equation is obtained as transient solution $v_{ptr}$.

$$v_{ptr} = \left[(v_{02}-P_0)\cos\omega_1(t-t_1) - \right. \tag{78}$$
$$\left. \frac{\{(1-\beta_1 CR_p)(v_{02}-P_0) - R_p(i_0-J_0)\}\{\sin\omega_1(t-t_1)\}}{\omega_1 CR_p}\right] \times$$
$$\exp(\beta_1 t_1)\exp(-\beta_1 t)$$

Where, when $$B_{1tr} = v_{o2} - P_0 \tag{79}$$

$$t' = t - t_1 \tag{80}$$

$$B_{2tr} = -\frac{(1-\beta_1 CR_p)(v_{02}-P_0) - R_p(i_0-J_0)}{\omega_1 CR_p} \tag{81}$$

then the following equation (82) is obtained.

$$v_{ptr} = (B_{1tr}\cos\omega_1 t' + B_{2tr}\sin\omega_1 t')\exp(-\beta_1 t') \tag{82}$$

Accordingly, equation (65) becomes as follows.

$$v_p = (E_1\cos\omega_s t + E_2\sin\omega_s t) + (B_{1tr}\cos\omega_1 t' + B_{2tr}\sin\omega_1 t')\exp(-\beta_1 t') \tag{83}$$

Next, the terms in the above equation (66) are defined as follows:

$$D_{1st} = \frac{E_1}{R_p} + \omega_s CE_2 \tag{84}$$

$$D_{2st} = -\omega_s CE_1 + \frac{E_2}{R_p} \tag{85}$$

$$D_{1tr} = \left(\frac{1-\beta_1 CR_p}{R_p}\right)B_{1tr} + \omega_1 CB_{2tr} \tag{86}$$

$$D_{2tr} = -\omega_1 CB_{1tr} + \left(\frac{1-\beta_1 CR_p}{R_p}\right)B_{2tr} \tag{87}$$

As a result, the following equation (88) is obtained for current i:

$$i = (D_{1st}\cos\omega_s t + D_{2st}\sin\omega_s t) + (D_{1tr}\cos\omega_1 t' + D_{2tr}\sin\omega_1 t')\exp(-\beta_1 t') \tag{88}$$

Current $i_s$ is obtained as the following equation.

$$i_s = C_c\frac{dv_1}{dt} + i = \omega_s C_c E'_m\cos\omega_s t + i \tag{89}$$

(Expansion Phase)

During expansion, diode D turns OFF, ending the impression of the left cardiac ventricle pressure e on the cathode side of the diode D circuit. As a result, the current flowing through capacitance $C_c$ has the same absolute value and the opposite polarity of current i. Accordingly, voltage $v_1$ may be expressed by the above equation (1), while currents i and $i_c$ may be expressed by the following equations, respectively.

$$i = -C_c\frac{dv_1}{dt} \tag{90}$$

$$i_c = C\frac{dv_p}{dt} \tag{91}$$

Accordingly, voltage $v_p$ becomes $$v_p = R_p(i-i_c) = -R_p\left(C_c\frac{dv_1}{dt} + C\frac{dv_p}{dt}\right) \tag{92}$$

Further, since $i - i_c = i_p = v_p/R_p$, the following equation results.

$$i = \frac{v_p}{R_p} + C\frac{dv_p}{dt} \tag{93}$$

Substituting equation (93) into equation (1), and differentiating both sides of the obtained equation with respect to time t, the following equation is obtained.

$$\frac{dv_1}{dt} = LC\frac{d^3v_p}{dt^3} + \left(\frac{L}{R_p} + CR_c\right)\frac{d^2v_p}{dt^2} + \left(\frac{R_c}{R_p} + 1\right)\frac{dv_p}{dt} \quad (94)$$

Next, the following equation may be drawn from equations (90) and (93).

$$\frac{dv_1}{dt} = -\frac{\frac{v_p}{R_p} + C\frac{dv_p}{dt}}{C_c} \quad (95)$$

Further, the following equation may be obtained from equations (94) and (95).

$$LC\frac{d^3v_p}{dt^3}\left(\frac{L + CR_cR_p}{R_p}\right)\frac{d^2v_p}{dt^2} + \left(\frac{C_cR_c + C_cR_p + CR_p}{C_cR_p}\right)\frac{dv_p}{dt} + \left(\frac{1}{C_cR_p}\right)v_p = 0 \quad (96)$$

Accordingly, the is equation may be restarted as:

$$\frac{d^3v_p}{dt^3} + A_1'\frac{d^2v_p}{dt^2} + A_2'\frac{dv_p}{dt} + A_3'v_p = 0 \quad (97)$$

where:

$$A_1' = \frac{L + CR_cR_p}{LCR_p} \quad (98)$$

$$A_2' = \frac{C_cR_c + C_cR_p + CR_p}{LC_cCR_p} \quad (99)$$

$$A_3' = \frac{1}{LC_cCR_p} \quad (100)$$

Next, the following equation is obtained when $v_p = \exp(\lambda t)$ and substituted into equation (97).

$$(\lambda^3 + A_1\lambda^2 + A_2\lambda + A_3) \exp(\lambda t) = 0 \quad (101)$$

Next, the following definitions are provided.

$$p = \frac{A_1'^2}{9} - \frac{A_2'}{3} \quad (102)$$

$$q = -\frac{A_1'^3}{27} + \frac{A_1'A_2'}{6} - \frac{A_3'}{2} \quad (103)$$

$$u = (q + \sqrt{q^2 - p^3})^{1/3} \quad (104)$$

$$v = (q - \sqrt{q^2 - p^3})^{1/3} \quad (105)$$

$$\alpha' = -(u + v) + \frac{A_1'}{3} \quad (106)$$

$$\beta_2 = \frac{u+v}{2} + \frac{A_1'}{3} \quad (107)$$

$$\omega_2 = (u - v)\frac{\sqrt{3}}{2} \quad (108)$$

$$\lambda_1 = -\alpha' \quad (109)$$

$$\lambda_2 = -\beta_2 + j\omega_2 \quad (110)$$

$$\lambda_3 = -\beta_2 - j\omega_2 \quad (111)$$

Note that the oscillation mode is indicated when $(q^2 - p^3) > 0$.

Next, voltage $v_p$ is assumed according to the following equation.

$$v_p = b_1 \exp(-\alpha't) + b_2 \exp\{(-\beta_2 + j\omega_2)t\} + b_3 \exp\{(-\beta_2 - j\omega_2)t\} \quad (112)$$

As a result, current i may be expressed by the following equation after substituting equation (112) into equation (93).

$$i = g_0 b_1 \exp(-\alpha't) + (g_1 + jg_2)b_2 \exp\{(-\beta_2 + j\omega_2)t\} + (g_1 - jg_2)b_3 \exp\{(-\beta_2 - j\omega_2)t\} \quad (113)$$

where, $$g_0 = \frac{1 - \alpha'CR_p}{R_p} \quad (114)$$

$$g_1 = \frac{1 - \beta_2 CR_p}{R_p} \quad (115)$$

$$g_2 = \frac{\omega_2 CR_p}{R_p} \quad (116)$$

Accordingly, voltage $v_i$ becomes as follows from equation (113).

$$v_1 = -\frac{1}{C_c}\int i\,dt \quad (117)$$
$$= f_0 b_1 \exp(-\alpha't) + (f_1 + jf_2)b_2\exp\{(-\beta_2 + j\omega_2)t\} + (f_1 - jf_2)b_3\exp\{(-\beta_2 - j\omega_2)t\}$$

where, $$f_0 = \frac{g_0}{\alpha' C_c} \quad (118)$$

$$f_1 = \frac{\beta_2 g_1 - \omega_2 g_2}{(\beta_2^2 + \omega_2^2)C_c} \quad (119)$$

$$f_2 = \frac{\omega_2 g_1 + \beta_2 g_2}{(\beta_2^2 + \omega_2^2)C_c} \quad (120)$$

Next, for the purpose of simplifying calculations, time $t_2$ shown in FIG. 4 will be set to $t=0$. When voltage $v_1$, voltage $v_p$ and current i at $t=0$ are set respectively to $v_{01}$, $v_{02}$ and $i_0$, then the following expressions are obtained when the term t in equations (117), (112) and (113) is set to $t=0$.

$$v_{01} = f_0 b_1 + (f_1 + jf_2)b_2 + (f_1 - jf_2)b_3 \quad (121)$$

$$v_{02} = b_1 + b_2 + b_3 \quad (122)$$

$$i_0 = g_0 b_1 + (g_1 + jg_2)b_2 + (g_1 - jg_2)b_3 \quad (123)$$

Rewriting the second and third terms in equation (112), the following equation is obtained for voltage $v_p$.

$$v_p = b_1\exp(-\alpha't) + \{(b_2 + b_3)\cos\omega_2 t + j(b_2 - b_3)\sin\omega_2 t\}\exp(-\beta_2 t) \quad (124)$$
$$= B_0\exp(-\alpha't) + (B_1\cos\omega_2 t + B_2\sin\omega_2 t)\exp(-\beta_2 t)$$

Where, $$B_0 = b_1 = v_{02} - \frac{k_1 g_2 - k_2 f_2}{k_4 g_2 - k_3 f_2} \quad (125)$$

$$B_1 = b_2 + b_3 = \frac{k_1 g_2 - k_2 f_2}{k_4 g_2 - k_3 f_2} \tag{126}$$

$$B_2 = j(b_2 - b_3) = \frac{k_2 g_4 - k_1 f_3}{k_4 g_2 - k_3 f_2} \tag{127}$$

and $$k_1 = v_{01} - f_0 v_{02} \tag{128}$$

$$k_2 = i_0 - g_0 v_{02} \tag{129}$$

$$k_3 = g_1 - g_0 \tag{130}$$

$$k_4 = f_1 - f_0 \tag{131}$$

Next, the following equation is obtained for current i by substituting $v_p$ of equation (124) into equation 2.

$$i\, D_0 \exp(-\alpha' t) + (D_1 \cos \omega_2 t) \exp(-\beta_2 t) \tag{132}$$

Where, $$D_0 = \left(\frac{1 - \alpha' C R_p}{R_p}\right) B_0 \tag{133}$$

$$D_1 = \left(\frac{1 - \beta_2 C R_p}{R_p}\right) B_1 + \omega_2 C B_2 \tag{134}$$

$$D_2 = -\omega_2 C B_1 + \left(\frac{1 - \beta_2 C R_p}{R_p}\right) B_2 \tag{135}$$

Accordingly, from equation (132), voltage $v_1$ becomes:

$$v_1 = -\frac{1}{C_c} \int i\, dt \tag{136}$$
$$= H_0 \exp(-\alpha' t) + (H_1 \cos \omega_2 t + H_2 \sin \omega_2 t) \exp(-\beta_2 t)$$

Where, $$H_0 = \frac{D_0}{\alpha' C_c} \tag{137}$$

$$H_1 = \frac{\beta_2 D_1 + \omega_2 D_2}{(\beta_2^2 + \omega_2^2) C_c} \tag{138}$$

$$H_2 = \frac{-\omega_2 D_1 + \beta_2 D_2}{(\beta_2^2 + \omega_2^2) C_c} \tag{139}$$

In the preceding explanation, time $t_2$ was set to t=0. Therefore, a substitution of t→(t−$t_2$) is carried out in order to match the time scale. Voltage $v_1$, voltage $v_p$ and current i can be obtained as follows from equations (136), (124) and (132) respectively.

$$v_1 = H_0 \exp\{-\alpha'(t - t_2)\} + \{H_1 \cos \omega_2(t - t_2) + \tag{140}$$
$$H_2 \sin \omega_2(t - t_2)\} \exp\{-\beta_2(t - t_2)\}$$
$$= H_0 \exp\{-\alpha'(t - t_2)\} +$$
$$[H_m \sin\{\omega_2(t - t_2) + \phi_{21}\}] \exp\{-\beta_2(t - t_2)\}$$

$$v_p = B_0 \exp\{-\alpha'(t - t_2)\} + \{B_1 \cos \omega_2(t - t_2) + \tag{141}$$
$$B_2 \sin \omega_2(t - t_2)\} \exp\{-\beta_2(t - t_2)\}$$
$$= B_0 \exp\{-\alpha'(t - t_2)\} +$$
$$[B_m \sin\{\omega_2(t - t_2) + \phi_{22}\}] \exp\{-\beta_2(t - t_2)\}$$

$$i = D_0 \exp\{-\alpha'(t - t_2)\} + \{D_1 \cos \omega_2(t - t_2) + \tag{142}$$
$$D_2 \sin \omega_2(t - t_2)\} \exp\{-\beta_2(t - t_2)\}$$
$$= D_0 \exp\{-\alpha'(t - t_2)\} +$$
$$[D_m \sin\{\omega_2(t - t_2) + \phi_{23}\}] \exp\{-\beta_2(t - t_2)\}$$

Where, $$H_m = \sqrt{H_1^2 + H_2^2} \tag{143}$$

$$\phi_{21} = \tan^{-1} \frac{H_1}{H_2} \tag{144}$$

$$B_m = \sqrt{B_1^2 + B_2^2} \tag{145}$$

$$\phi_{22} = \tan^{-1} \frac{B_1}{B_2} \tag{146}$$

$$D_m = \sqrt{D_1^2 + D_2^2} \tag{147}$$

$$\phi_{23} = \tan^{-1} \frac{D_1}{D_2} \tag{148}$$

Here, current $i_s$ during the expansion phase is 0.

Next, a theoretical value for stroke volume SV will be obtained. Stroke volume SV is given by the area of current $i_s$ during the contraction phase, and thus may be obtained by integrating equation (89) for current $i_s$ over the range from $t_1$ to $t_2$. Namely:

$$SV = \int_{t_1}^{t_2} i_s dt \tag{149}$$
$$= \left(\frac{\omega_S C_C E_m' + D_{1st}}{\omega_S}\right)(\sin \omega_S t_2 - \sin \omega_S t_1) -$$
$$\frac{D_{2st}}{\omega_S}(\cos \omega_S t_2 - \cos \omega_S t_1) +$$
$$\frac{\exp\{-\beta_1(t_2 - t_1)\}}{\beta_1^2 + \omega_1^2}\{-(\beta_1 D_{1tr} + \omega_1 D_{2tr})\cos \omega_1(t_2 - t_1) +$$
$$(\omega_1 D_{1tr} - \beta_1 D_{2tr})\sin \omega_1(t_2 - t_1)\} +$$
$$\frac{\beta_1 D_{1tr} + \omega_1 D_{2tr}}{\beta_1^2 + \omega_1^2}$$

Figure 12:
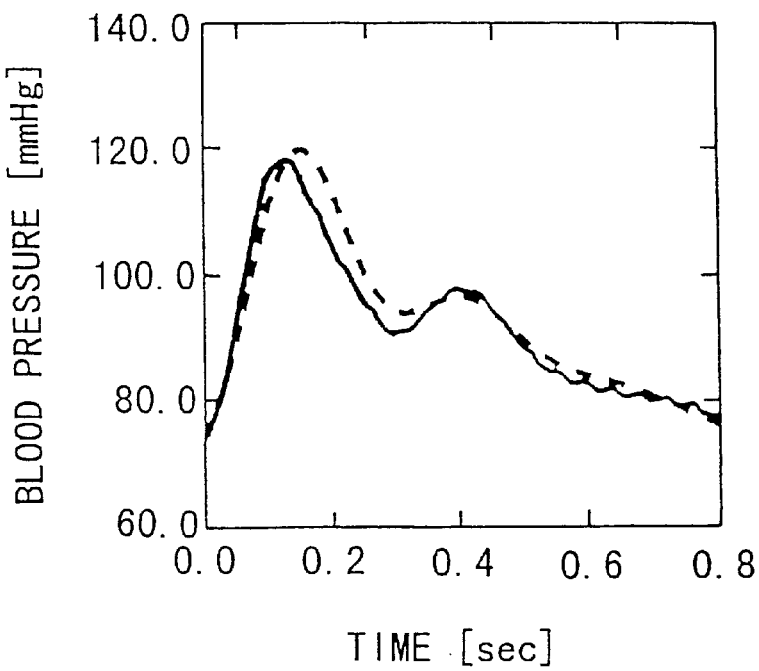
FIG. 12 is a waveform diagram showing the superimposition of the radius artery waveform obtained through calculation processing and the radius artery waveform obtained through averaging processing in the pulsewave analysis device.

An explanation of the operation of the pulsewave analysis device according to the present embodiment will now be made. FIGS. 6 through 10 are flow charts showing the operation of this pulsewave analysis device. FIG. 11 is a waveform diagram of the average waveform which is obtained as a result of the averaging processing described above. FIG. 12 is a waveform diagram contrasting a radius artery waveform obtained by parameter calculation processing, to be described below, and the average waveform which is obtained as a result of averaging. An explanation of the pulsewave analysis device's operation now follows, with reference given to these figures.

① Pulsewave Readout Processing

In order to evaluate the circulatory state parameters in a test subject, an diagnostician attaches the cuff S1 and pressure sensor S2 to the test subject as shown in FIG. 2, and inputs a start-measurement command via keyboard 5. In response to this command, microcomputer 4 sends an indication to pulsewave detector 1 to measure the pulsewave. As a result, pulsewave detector 1 detects the radius artery pulsewave, and A/D converter 3 outputs a time-series digital signals showing this radius artery pulsewave. Microcomputer 4 takes up the digital signals in the waveform memory housed therein over a fixed interval of time (approximately 1 minute). In this manner, the radius artery waveform for a plurality of beats is taken up in waveform memory.

② Averaging Processing

Next, at each beat, microcomputer 4 superimposes the radius artery waveforms over a plurality of beats, and obtains the average waveform per beat over the aforementioned fixed interval of time. Then, this average waveform is stored in the internal memory as a representative waveform of the radius artery waveforms (Step S1). An example of a thus-produced representative waveform WI of the average waveform is shown in FIG. 11.

③ Uptake of Stroke-volume Data Processing

Next, microcomputer 4 sends an indicator to measure stroke volume to stroke-volume measurer 2. As a result, stroke-volume measurer 2 measures the stroke volume in the test subject, with the measured result taken up by temporary memory in microcomputer 4 (Step S2).

④ Parameter Calculation Processing

First, the four circulatory state parameter excluding capacitance $C_c$ are determined based on the lumped four parameter model.

Figure 7:
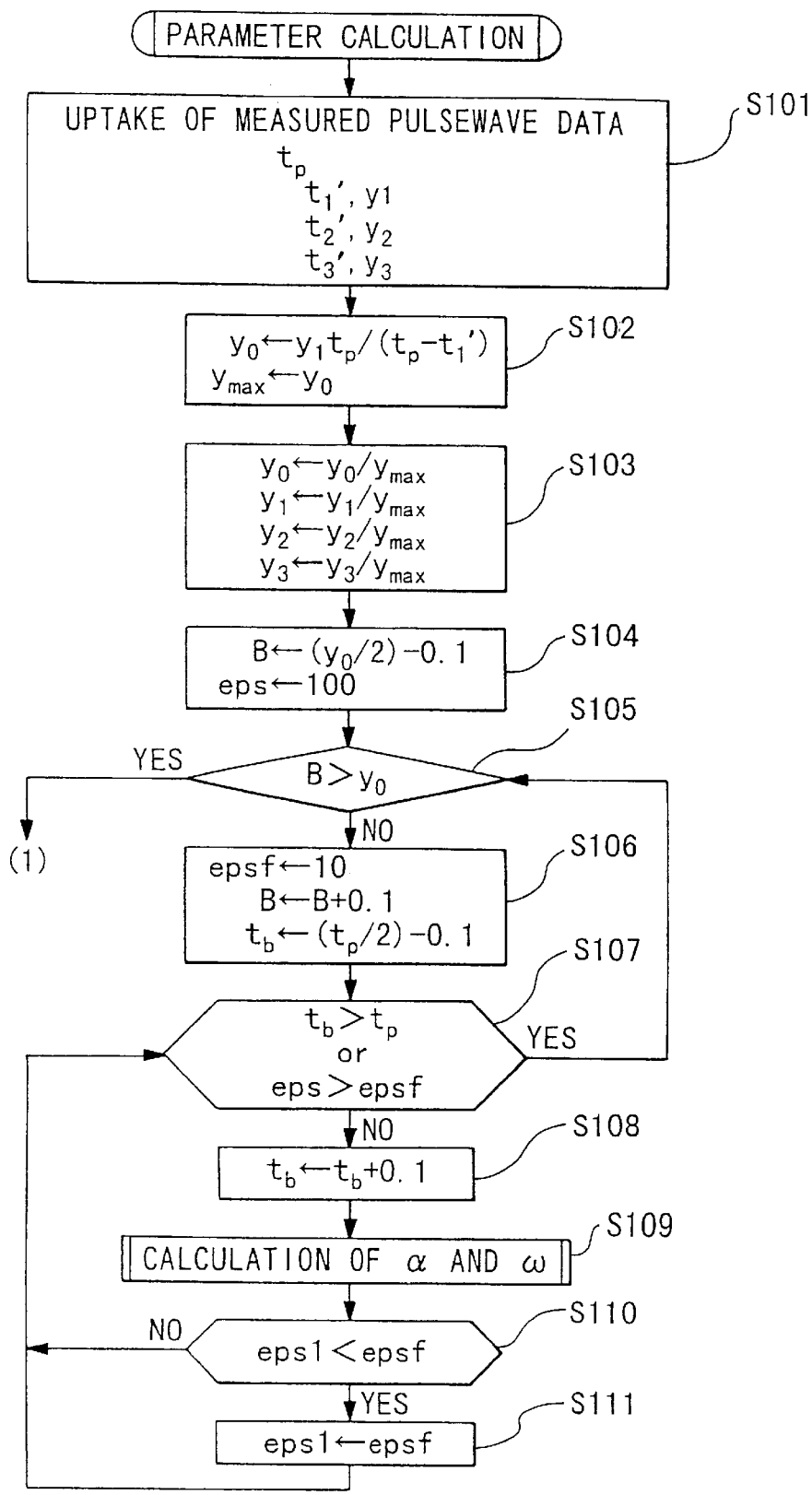
FIG. 7 is a flow chart showing the processing operations for parameter calculation in the pulsewave analysis device.
Figure 8:
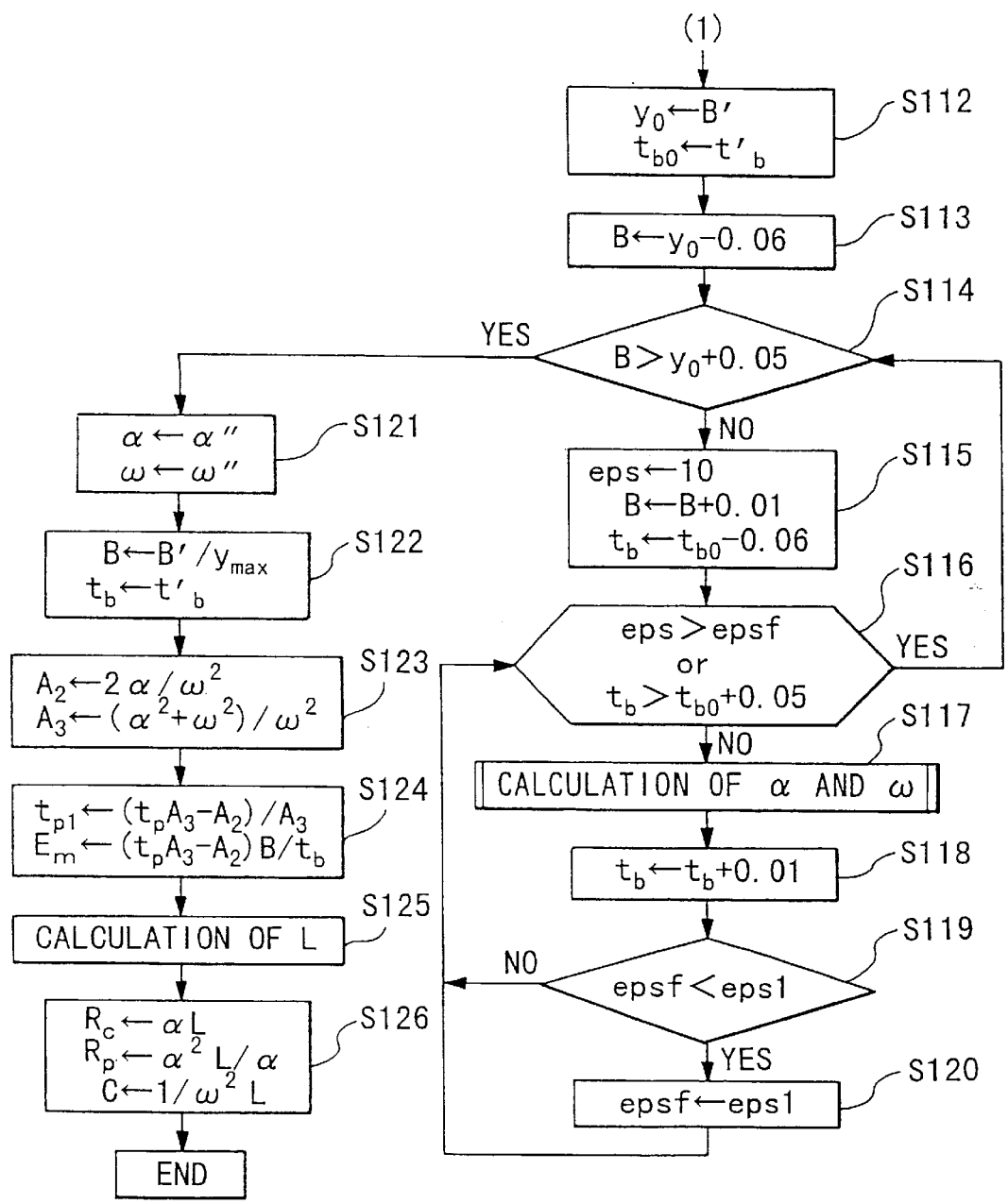
FIG. 8 is a flow chart showing the processing operations for parameter calculation in the pulsewave analysis device.
Figure 9:
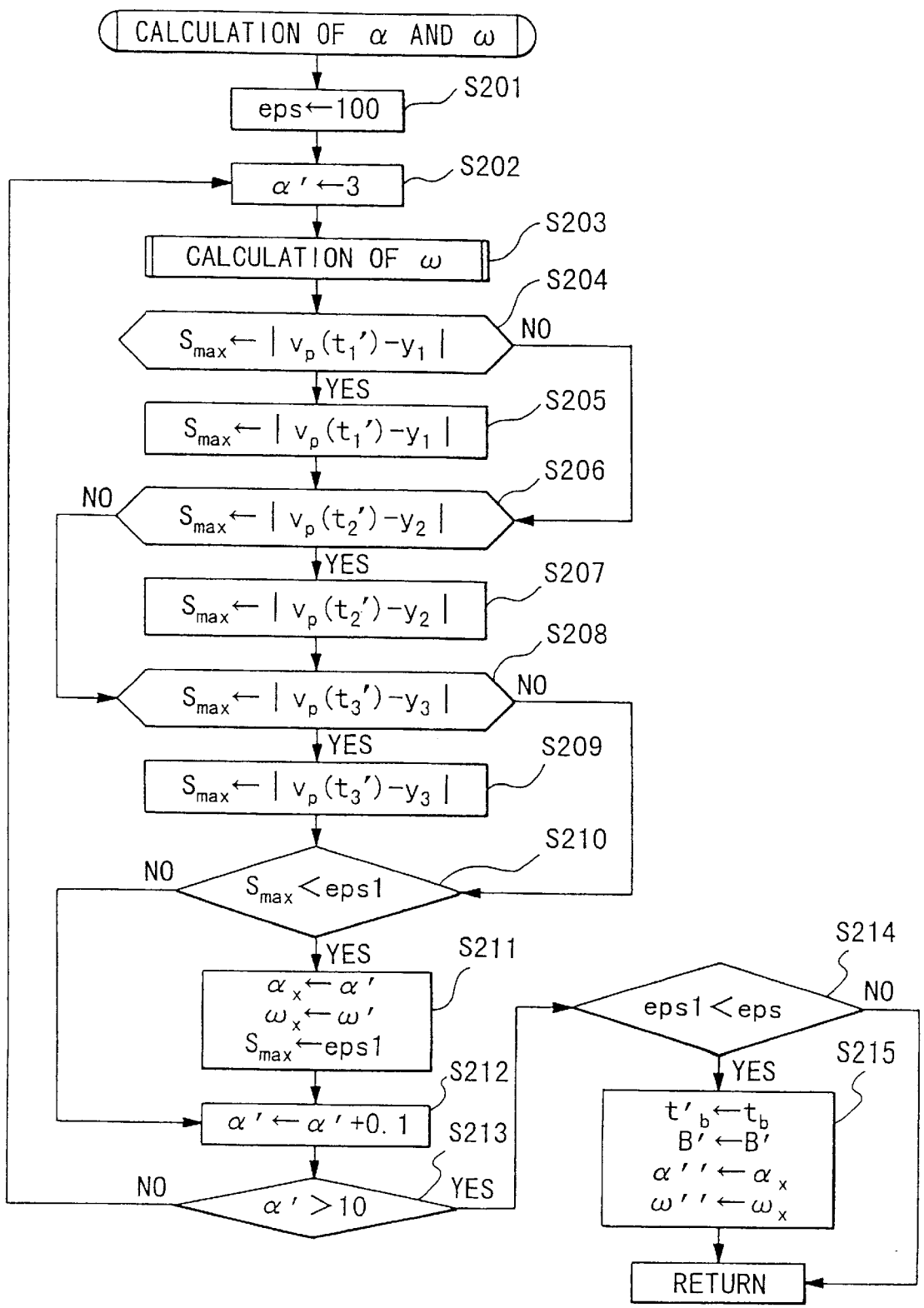
FIG. 9 is a flow chart showing the processing operations for calculating α and ω in the pulsewave analysis device.
Figure 10:
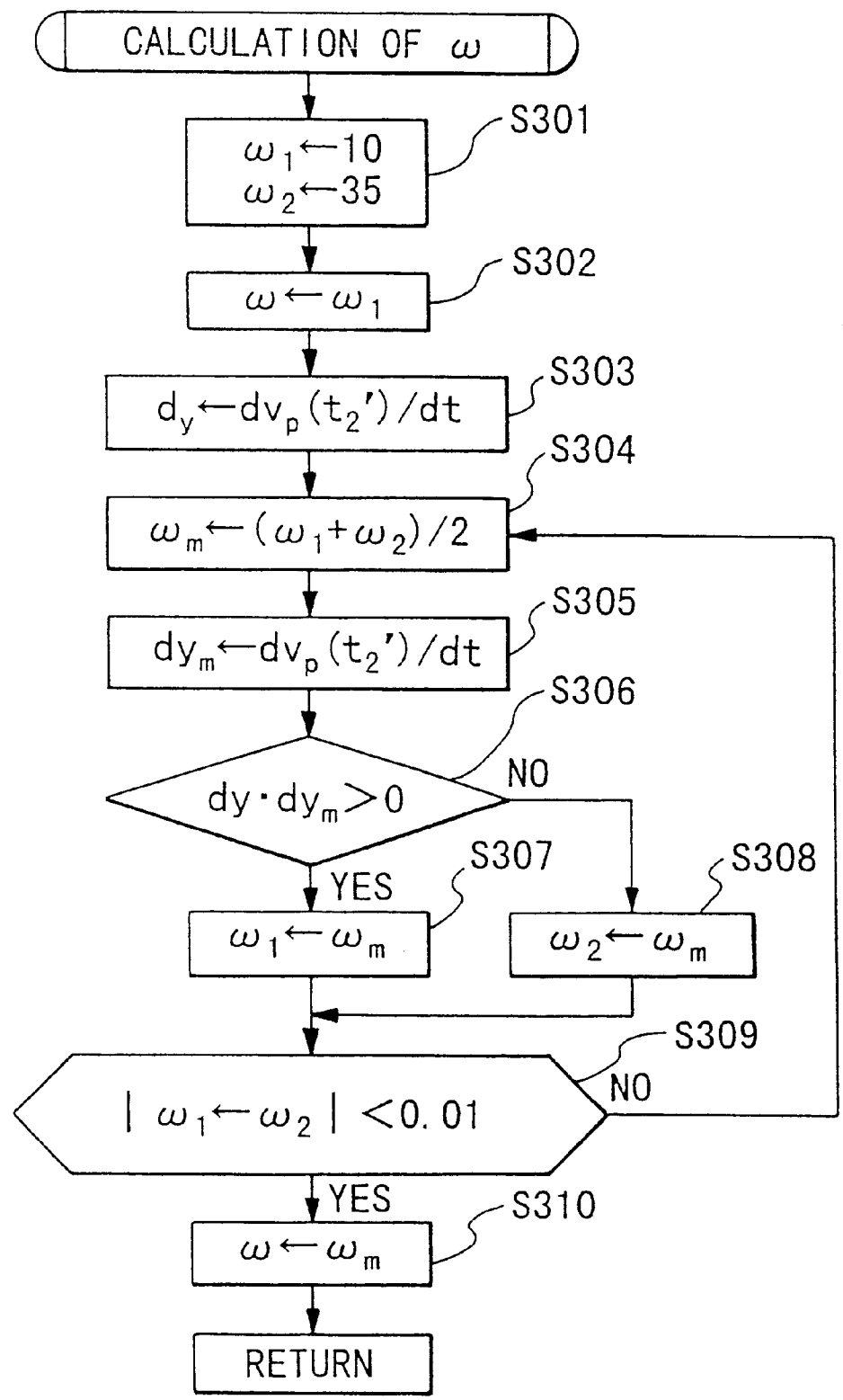
FIG. 10 is a flow chart showing the processing operations for calculating ω in the pulsewave analysis device.

Processing in microcomputer 4 proceeds to Step S3, executing the parameter calculation processing routine shown in FIGS. 7 and 8. At this time, the routine shown in FIG. 9 for calculating α and ω is carried out (Steps S109, S117). Accompanying the execution of the routine for calculating α and ω, the routine for calculating ω shown in FIG. 10 is carried out (Step S203.)

An explanation will now be made of the details of the processing carried out in the routines mentioned above. First, as shown in FIG. 11, microcomputer 4 determines for the average waveform of the radius artery the time $t_1'$ and blood pressure value $y_1$ corresponding to a first point P1 at which blood pressure reaches a maximum value; the time $t_2'$ and blood pressure value $y_2$ corresponding to a second point at which blood pressure falls subsequent to the first point; the time $t_3'$ and blood pressure value ye corresponding to a third point P3 which is the second peak point; and the time $t_p$ per beat and diastolic pressure value $E_{min}$ (corresponding to the first term in equations (3) and (4) above) (Step S101).

In the case where it is difficult to discriminate between second point P2 and third point P3 when the pulsewave is gentle, then the times at the second point and the third point are assumed to be $t_2'=2t_1'$ and $t_3'=3t_1'$, respectively.

Figure 13:
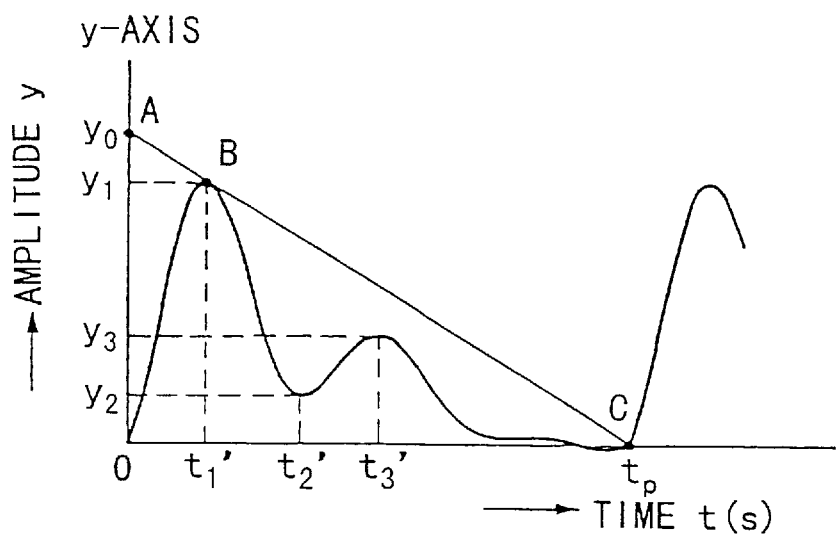
FIG. 13 is a diagram for explaining the details of the normalizing processing which is applied to the radius artery waveform obtained as result of averaging processing in the pulsewave analysis device.

Next, in order to simplify the processing, normalization of blood pressure values $y_1$ to $y_3$ is carried out using blood pressure value $y_0$ at point A shown in FIG. 13 (Steps S102, S103), and the value at point B is initially set to $(y_0/2)-0.1$.

Next, optimal values for B, $t_b$, α and ω are determined according to the following process.

a) B is varied within the range $[(y_0/2)\sim y_0]$ and $t_b$ is varied within the range $[(t_p/2)\sim t_p]$, at +0.1 intervals in both cases. The α and ω for which $|v_p(t_1')-y_1|$, $|v_p(t_2')-y_2|$ and $|v_p(t_3')-y_3|$ are minimized are determined for each B and $t_b$.

b) From among the B, $t_b$, α and ω values obtained in a) above, the B, $t_b$, α and ω for which $|v_p(t_1')-y_1|$, $|v_p(t_2')-y_2$ and $|v_p(t_3')-y_3|$ are minimized are determined.

c) Using the B and $t_b$ obtained in b) above as standards, the processing in a) and b) is carried out again for B within in the range of B±0.05 and for $t_b$ within the range of t±0.05.

d) When carrying out the processing in a) through c) above, α is varied by 0.1 increments within the range from 3 to 10, and optimal ω values are calculated for each α. Next, for each α, dichotomy is used to obtain the ω at which $dv_p(t_2')/dt=0$ (see the flow chart in FIG. 10). When calculating the value of $v_p$ in the above processing, the initial value $v_{01}$ in equation (33) is set to zero. As a result of the preceding processing, the final values of B, $t_b$, α and ω are determined.

e) $t_{p1}$, $E_m$, and $E_0$ are calculated based on equations (28) through (30) and (44) through (46) (Steps S123, S124).

f) The value of L is calculated based on the measured stroke volume, using equation (50) (Step S125), and the remaining parameters $R_c$, $R_p$, and C are obtained from equations (44) through (46) (Step S126).

Next, based on the lumped five parameter model, the final circulatory parameter of capacitance $C_c$ is determined. For this purpose, methods may be considered wherein capacitance $C_c$ is determined so that the calculated value and the actual measured value of stroke volume SV are equivalent, and wherein capacitance $C_c$ is determined so that the calculated value and the actual measured value of the diastolic pressure of the pulsewave are equivalent. Each of these methods will be explained separately.

④-1. Method to Determine Capacitance $C_c$ (Aortic Compliance) so that the Calculated and Measured Values of Stroke Volume are Equivalent An explanation will first be made of a specific method for determining capacitance $C_c$ so that the calculated and measured value of stroke volume SV are equivalent.

First, the value of capacitance $C_c$ is estimated as in the following equation, based on the value of capacitance C which was calculated using the lumped four parameter model. Moreover, values obtained using the lumped four parameter model are employed for the values of the other circulatory state parameters, $R_c$, $R_p$, C and L.

$$C_c=10 \cdot C \qquad (150)$$

Next, stroke volume SV is calculated according to equation (149), using these circulatory state parameters. In this case, the time $t_s$ of rising pressure in the left cardiac ventricle is estimated according to the following equation, from the time $t_p$ of one beat which was obtained from the lumped four parameter model.

$$t_s=(1.52-1.079t_p)t_p \qquad (151)$$

Figure 14:
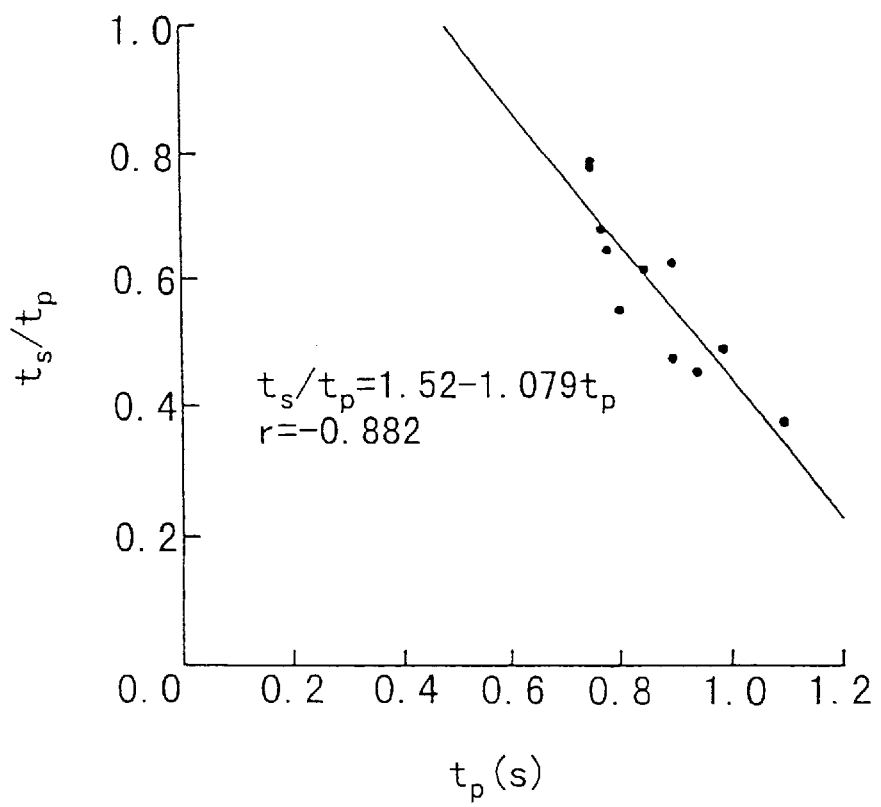
FIG. 14 is a diagram showing the correlation between the time $t_s$ of increasing pressure in the left cardiac ventricle and the time $t_p$ of one beat.

This relational equation is an experimental equation obtained as a result of measuring the contraction time of the left cardiac ventricle using a heart echo. As shown in FIG. 14, −0.882 is obtained as the correlation coefficient. Additionally, the value obtained using the lumped four parameter model is employed for systolic pressure $E_m'$ (see equations (22) and (28)). In addition, time $t_1$ and $t_2$ are obtained from the relationship: left cardiac ventricle pressure=aortic pressure. Moreover, since $v_{02}$ and $i_0$ are the values of $v_p$ and i at $t=t_1$, $t_1$ is substituted for t in equations (83) and (88), to obtain $v_{02}$ and $i_0$.

The value of capacitance $C_c$ is determined so that the calculated value for stroke volume SV obtained as above is equivalent to the measured value taken up from stroke-volume measurer 2. In other words, the value of capacitance $C_c$ is varied within in a fixed range starting from an initial value obtained from equation (150). Then, the measured value of stroke volume and the value which was calculated from each capacitance $C_c$ values is compared, and a check is made to see if the integer part of the measured and calculated values are equivalent. If the integer parts are equivalent, then the measured and calculated values of capacitance are deemed equal, capacitance $C_c$ is determined, and parameter calculation processing is terminated.

On the other hand, if no coincidence is observed in the measured and calculated values of stroke volume merely by adjusting the value of capacitance $C_c$, then from armong the adjusted capacitance $C_c$ values, the capacitance $C_c$ value at which the difference between the measured and calculated values for stroke volume is minimized is selected as the final value for capacitance $C_c$. Next, the value of systolic pressure $E_m'$ is varied by 1 mmHg within a range of ±3 mmHg, and a check is made for the presence of a coincidence between the calculated and measured values for stroke volume in the same manner as described above. If a systolic pressure value $E_m'$ is present at which coincidence is observed, then that value is set as the final systolic pressure value $E_m'$, and parameter calculation processing is terminated.

If no coincidence is observed between the measured and calculated values for stroke volume even after adjusting the value of systolic pressure $E_m'$, then the value of resistance $R_p$ is adjusted. Then, from among the adjusted systolic pressure values $E_m'$, the value at which the difference in the measured and calculated values for stroke volume is minimized is set as the final systolic pressure value $E_m'$. Next, resistance $R_p$ is increased or decreased by intervals of 10[dyn·s/cm$^5$], for example, with the $R_p$ value at which the difference between the measured and calculated values for stroke volume is minimized selected as the final resistance $R_p$ value.

Figure 31:
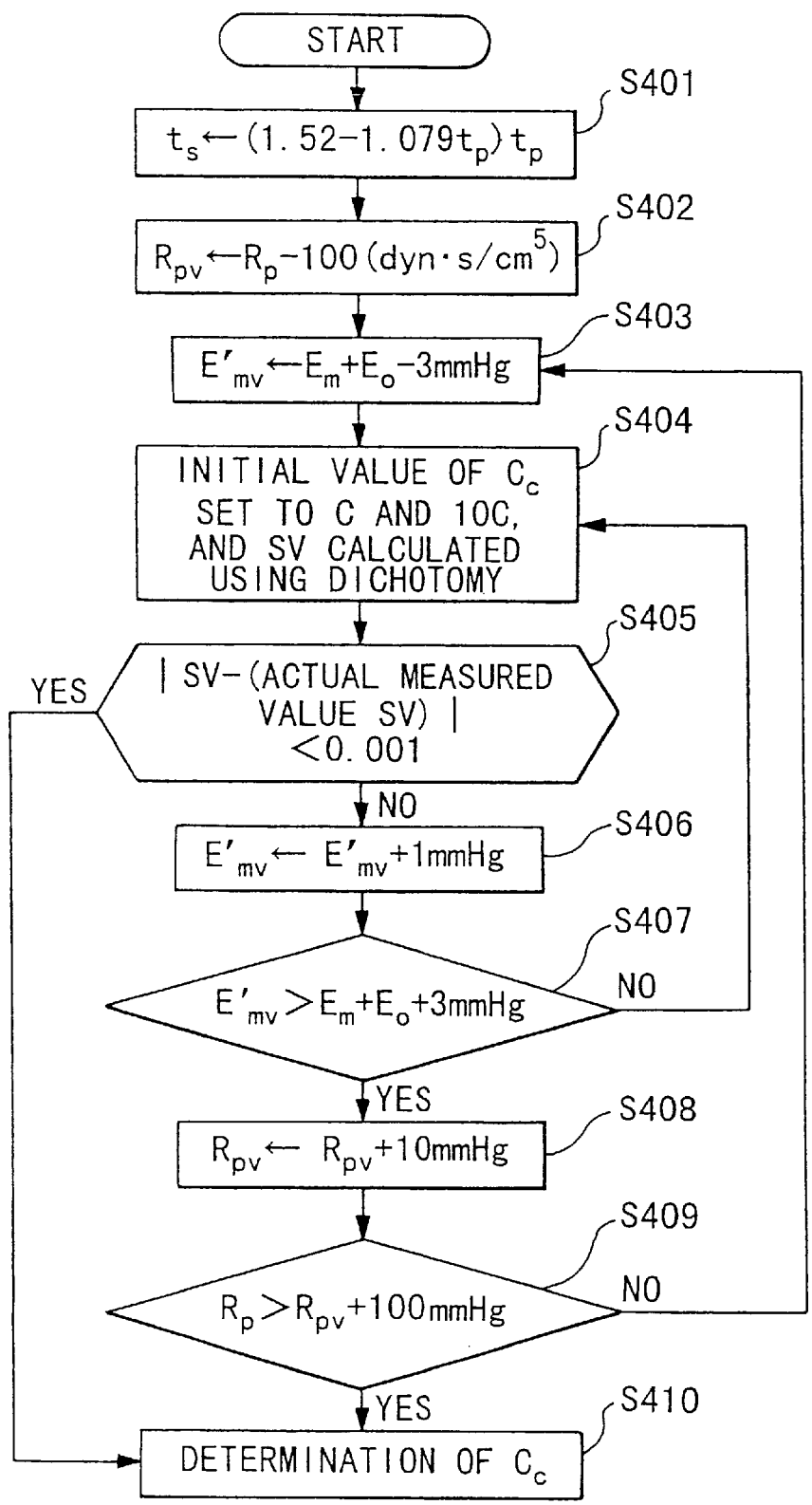
FIG. 31 is a flow chart of the program for obtaining capacitance $C_c$.

An example of a flow chart for realizing the above-described process is shown in FIG. 31. Note that with respect to the parameters which are varied within a fixed range in the program, a subscript "v" has been added to indicate the original parameters.

④-2. Method for Determining Capacitance $C_c$ so that the Diastolic Pressures of the Calculated Pulsewave and the Measured Pulsewave are Equivalent Next, an explanation will be made of a method for determining capacitance $C_c$ so that the diastolic pressures of the calculated pulsewave and the actual measured pulsewave are equivalent.

In this method, a contraction period QT is first obtained in advance from the test subject's electrocardiogram. Next, with respect to this contraction period QT, the time $t_sv$ during which pressure in the left cardiac ventricle is rising is varied by intervals of 0.01 secs within the range from [QT+0.1(sec)] to [QT+0.2(sec)]. At the same time, systolic pressure $E_mv'$ is varied by intervals of 1 mmHg over the range from [$E_0+E_m-20$ (mmHg)] to [$E_0+E_m+20$ (mmHg)].

In other words, the total number of combinations of each value of time $t_sv$ of rising pressure in the left cardiac ventricle and systolic pressure $E_mv'$ is 451. A capacitance $C_c$ is calculated for these combinations so that the diastolic pressure values of the calculated pulsewave and the measured pulsewave are equivalent.

Figure 32:
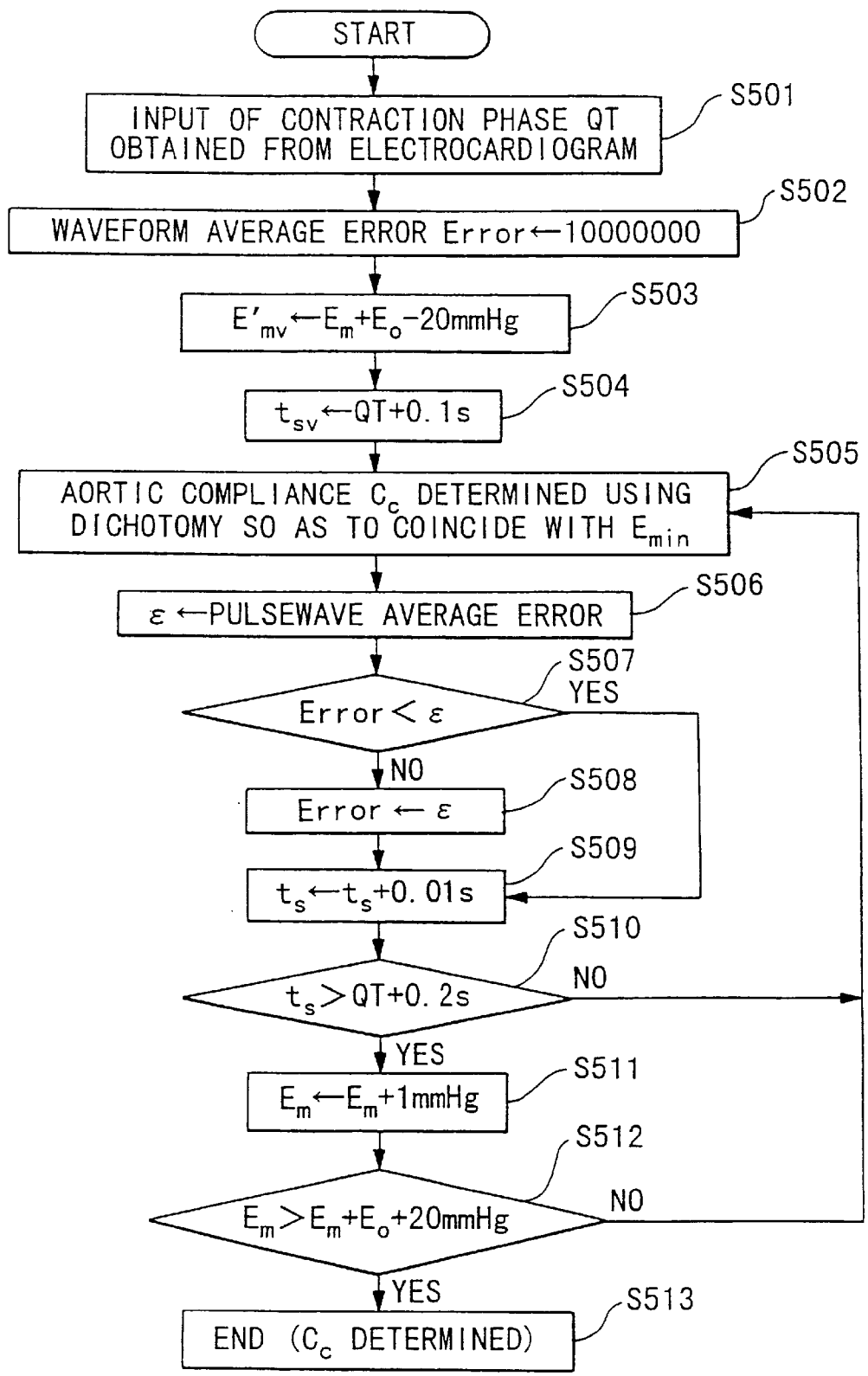
FIG. 32 is a flow chart of another program for obtaining capacitance $C_c$.

Next, the sampling value for the calculated pulsewave in each combination is defined as $P_1(t)$ and the sampling value for the actual measured pulsewave in each combination is defined as $P_2(t)$, and the average deviation ε of the waveform in each combination is obtained from the following equation. The capacitance $C_c$ (aortic compliance) at which this waveform average deviation ε is minimized is employed. An example of a flowchart for realizing the above-described process is shown in FIG 32.

$$\varepsilon = \sum_{t=0}^{t_p} \frac{|P_2(t) - P_2(t)|}{N} \quad (152)$$

In this manner, then, the circulatory state parameters at which the measured and calculated values of stroke volume are equivalent are all determined.

⑤ First Output Processing

Once the above-described process for calculating the parameters is completed, microcomputer 4 outputs the circulatory state parameters L, C, $C_c$, $R_c$, and $R_p$ to sequential output device 6 (Step S4).

The values of circulatory state parameters calculated from the radius artery waveform in the case where the test subject is a 32 year old male are shown below.

| | |
|---|---|
| Capacitance $C_c$ = | 0.001213 [cm$^5$/dyn] |
| Electric resistance $R_c$ = | 98.768 [dyn·s/cm$^5$] |
| Inductance L = | 15.930 [dyn·s$^2$/cm$^5$] |
| Capacitance C = | 0.0001241 [cm$^5$/dyn] |
| Electric resistance $R_p$ = | 1300.058 [dyn·s/cm$^5$] |
| Time $t_s$ of rising pressure in left cardiac ventricle = | 0.496 [s] |
| Time $t_p$ of one beat = | 0.896 [s] |
| Stroke volume SV = | 83.6 [cc/beat] |
| Systolic pressure $E_m'$ = | 117.44 [mmHg] |

As shown in FIG. 12, there is good coincidence between the measured waveform of the radius artery and the calculated waveform of the radius artery obtained from the calculated parameters.

⑥ Second Output Processing

In Step S4, the pressure waveform of the aorta is obtained based on the values of the circulatory state parameters L, C, $C_c$, $R_c$, and $R_p$. Namely, by employing equation (51) during the contraction phase and equation (140) during the expansion phase, the waveform of voltage $v_1$ is calculated for one beat only (i.e., time 0~time $t_p$ or time $t_1$~time ($t_1+t_p$)). Then, the calculated waveform is output to output device 6, with the pressure waveform of the aorta displayed. Next, the value of the obtained waveform of the proximal portion of the aorta at time $t_1$ is calculated from these equations, and this calculated value is defined as the diastolic pressure value $E_0$. The thus obtained systolic pressure value $E_m'$ is relayed to output device 6 together with the diastolic pressure value, and these values are displayed on output device 6.

Accordingly, by means of the present embodiment, it is possible to display each of the circulatory state parameters, as well as the systolic pressure, diastolic pressure and the pressure waveform of the aorta at the center of the arterial system, for the test subject or diagnostician.

Further, since equation (51) indicates the pressure waveform at the left cardiac ventricle, the pressure waveform of the left cardiac ventricle may be displayed on output device 6 in place of the pressure waveform of the aorta, as the pressure waveform at the center of the arterial system.

<Embodiment 2>

In the preceding first embodiment, the values of the circulatory state parameters were calculated from the radius artery waveform and the stroke volume. However, as explained above, in order to carry out a detection of stoke volume, it is necessary to attach cuff S1 to the test subject, subjecting the subject to some inconvenience. Accordingly, this embodiment provides for an estimation of blood pressure values at the center of the arterial system by focusing attention on a change in aortic pressure based on the shape of the radius artery waveform, and using distortion to represent the shape of the waveform. In other words, in this embodiment, the circulatory state parameters are derived based on distortion d which is obtained from the radius artery waveform.

First, in the same manner as in the first embodiment, microcomputer 4 carries out ① pulsewave readout and ② averaging, to obtain the average waveform per beat for the radius artery waveform. Next, a Fourier analysis of the pulsewave is performed by carrying out a fast Fourier transform (FFT) on the average waveform. Next, the fundamental wave's amplitude $A_1$, the second harmonic wave's amplitude $A_2$, the third harmonic wave's amplitude $A_3$, ... to the nth harmonic wave's amplitude $A_n$ are obtained from the frequency spectrum obtained as a result of this analysis. Here, the value of n (which is a natural number) is optimally determined after taking into consideration the size of the amplitude of the harmonic waves. Based on these amplitude values, then, distortion d defined by the following equation is calculated.

$$\text{distortion } d = \frac{(A_2^2 + A_3^2 + \cdots + A_n^2)^{1/2}}{A_1} \quad (153)$$

Next, the circulatory state parameters are estimated from the obtained distortion d. This estimation is carried out based on the understanding that there is a correlation in the degree of correspondence between the distortion of the radius artery waveform and each of the values of the circulatory state parameters. Namely, distortion d and circulatory state parameters are measured in advance for a number of test subjects, and a relational equation between distortion and the circulatory state parameters is derived. Examples of correlations obtained as a result of measuring distortion and the circulatory state parameters $R_c$, Rp, L and C are shown in FIGS. 25 through 28. Aortic compliance $C_c$ is not shown in these figures, however a correlation coefficient and a relational equation therefor may be obtained in the same manner as for the other four parameters.

Based on distortion d calculated from the above equation (153) and the relational equations shown in each of FIGS. 25 through 28, the circulatory state parameters of $R_c$, $R_p$, L, C, and $C_c$ are calculated. Next, output processing in steps ⑤ and ⑥ of the first embodiment are carried out in the same manner, to obtain the waveform of one beat of the pressure waveform of the aorta from the calculated circulatory state parameters. At the same time, diastolic pressure value $E_0$ and systolic pressure value $E_m$ at the proximal portion of the aorta are calculated and displayed on output device 6.

<Embodiment 3>

In this embodiment, in addition to systolic and diastolic pressure values at the proximal portion of the aorta, the workload on the heart (hereinafter, referred to as "cardiac workload") is calculated from the blood pressure waveform at the proximal portion of the aorta which is obtained as described above, and is displayed.

Cardiac workload, one indicator showing the load on the heart, is defined as the product of stroke volume and aortic pressure, and is the result of converting stroke volume per minute to workload.

Here, stroke volume is defined as the volume of blood flow sent out from the heart at each pulse, and corresponds to the area of the waveform of blood flow from the heart. Stroke volume is correlated with the area of contraction phase of the pressure waveform of the aorta, and may be obtained by applying the contraction phase area method on the pressure waveform of the aorta.

Figure 29:
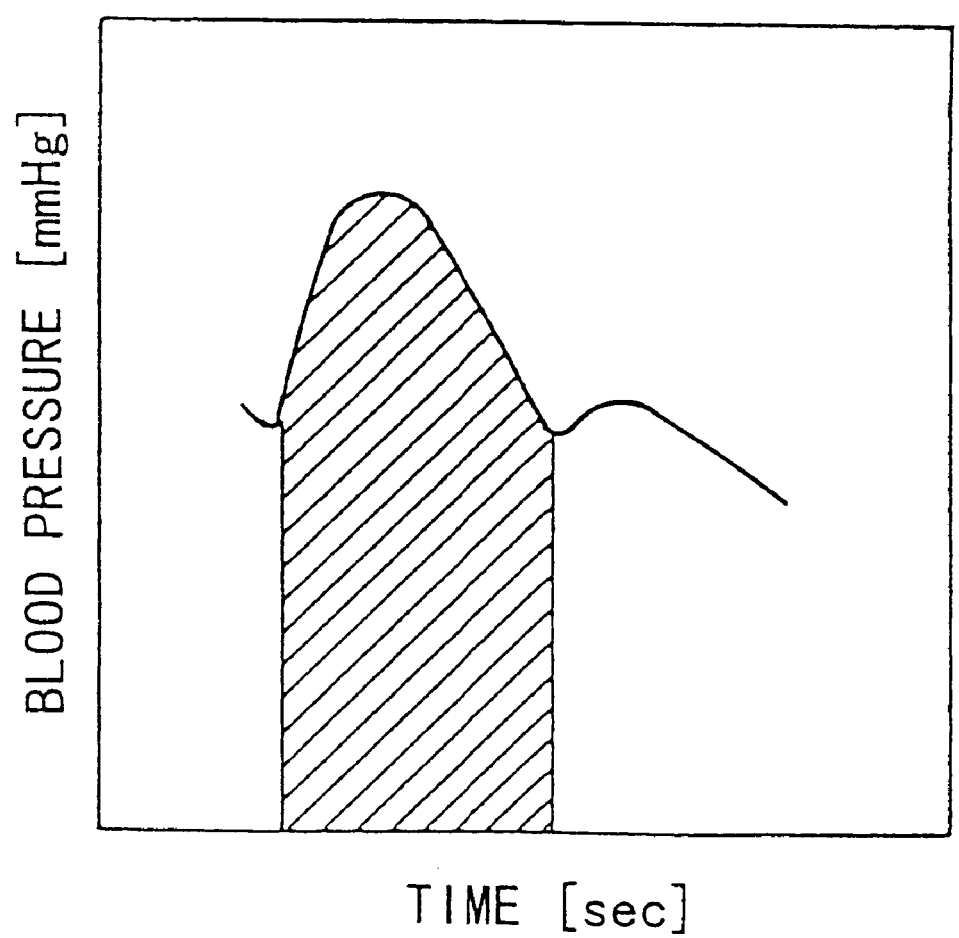
FIG. 29 is a diagram for explaining the contraction phase area method.
Figure 30:
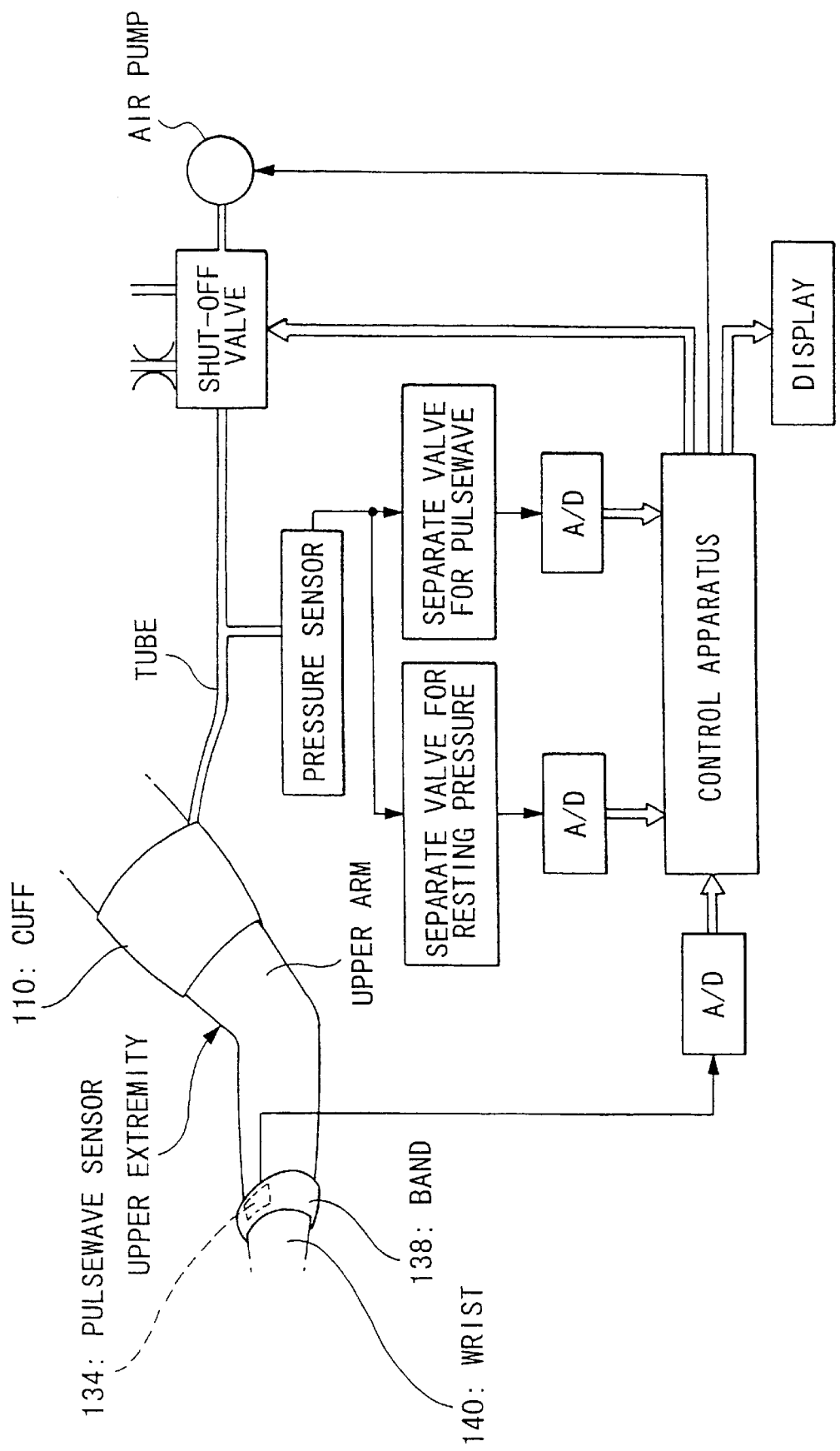
FIG. 30 is a diagram showing the structure of a sphygmomanometer employing the conventional technology.

In other words, the area S under the portion of the pulse waveform corresponding to a contraction phase in the heart is calculated. Explained in terms of the pulse waveform in FIG. 29, this is the area of the region from where the pulsewave is rising to where it notches, as indicated by the hatching. Next, stroke volume SV is calculated using the following equation, where K indicates a specific constant.

Stroke volume [ml]=area $S$ [mmHg·s]×$K$

Cardiac stroke volume is defined as the volume of blood flow sent out from the heart per minute. Accordingly, cardiac stroke volume can be obtained by converting stroke volume to minutes. In other words, cardiac stroke volume may be obtained by multiplying stroke volume by heart rate.

In this embodiment, in the output processing in ⑤ of the first and second embodiments, microcomputer 4 calculates the cardiac workload based on the pressure waveform calculated for the left cardiac ventricle, and displays this result on output device 6. The other processing is equivalent to the preceding embodiments, and an explanation thereof will thus be omitted.

Microcomputer 4 calculates cardiac workload $W_s$ according to the process shown below.

First, $w_s$ is defined as the product of $e \cdot i_s$, and may be calculated as follows from equations (51), (88), and (89).

$$w_s = e \cdot i_s \quad (154)$$
$$= \omega_s C_c E_m'^2 \sin\omega_s t \cos\omega_s t +$$
$$E_m' \sin\omega_s t (D_{1st}\cos\omega_s t + D_{2st}\sin\omega_s t) +$$
$$E_m' \sin\omega_s t (D_{1tr}\cos\omega_1 t + D_{2tr}\sin\omega_1 t)\exp(-\beta_1 t')$$

Setting the first, second and third terms in equation (154) to $w_1$, $w_2$, and $w_3$, respectively, these terms may be rewritten as follows.

$$w_1 = \frac{\omega_s C_c E_m'^2}{2} \sin 2\omega_s t \quad (155)$$

$$w_2 = \frac{E_m'}{2} \{D_{1st}\sin 2\omega_2 t - D_{2st}(\cos 2\omega_s t - 1)\} \quad (156)$$

$$w_3 = \frac{E_m'}{2} [D_{1tr}\{\sin(\omega_s t + \omega_1 t') + \sin(\omega_s t - \omega_1 t')\} - \quad (157)$$
$$D_{2tr}\{\cos(\omega_s t + \omega_1 t') - \cos(\omega_s t - \omega_1 t')\}]\exp(-\beta_1 t')$$

Next, using equation (80), the following expressions are defined:

$$\omega_s t + \omega_1 t' = \omega_s t \omega_1 (t - t_1) = (\omega_s + \omega_1)t - \omega_1 t_1 = \omega_a t - \Phi \quad (158)$$

$$\omega_s t - \omega_1 t' = (\omega_s - \omega_1)t + \omega_1 t_1 = \omega_b t + \Phi \quad (159)$$

Namely, $$\omega_a = \omega_s + \omega_1 \quad (160)$$

$$\omega_b = \omega_s - \omega_1 \quad (161)$$

$$\Phi = \omega_1 t_1 \quad (162)$$

In this case, then, equation (157) becomes as follows:

$$w_3 = \frac{E_m'}{2} [D_{1tr}\{\sin(\omega_a t - \Phi) + \sin(\omega_b t + \Phi)\} - \quad (163)$$
$$D_{2tr}\{\cos(\omega_a t - \Phi) - \cos(\omega_b t + \Phi)\}]\exp(-\beta_1 t')$$

Next, $W_1$, $W_2$, and $W_3$ are respectively defined as follows, and the following equation is derived from equations (155), (157) and (163).

$$W_1 = \int w_1 dt \quad (164)$$

$$= -\frac{C_c E_m'^2}{4} \cos 2\omega_s t$$

$$= \frac{C_c E_m'^2}{4}(1 - \cos^2 \omega_s t)$$

$$W_2 = \int w_2 dt \quad (165)$$

$$= \frac{E_m'}{2}\left\{-\left(\frac{D_{1st}}{2\omega_s}\right)\cos 2\omega_2 t - D_{2st}\left(\sin\frac{2\omega_s t}{2\omega_s} - t\right)\right\}$$

$$= \left(\frac{E_m'}{4\omega_s}\right)\{(D_{1st} + 2D_{2st}\omega_s t) -$$

$$2\cos\omega_s t(D_{1st}\cos\omega_s t + D_{2st}\sin\omega_s t)\}$$

$$W_3 = \int w_3 dt \quad (166)$$

$$= \frac{E_m'}{2}\left\{\frac{(-\omega_a D_{1tr} + \beta_1 D_{2tr})\cos(\omega_a t - \Phi) -}{\beta_1^2 + \omega_a^2} + \frac{-(\omega_b D_{1tr} + \beta_1 D_{2tr})\cos(\omega_b t + \Phi) +}{\beta_1^2 + \omega_b^2}\right\}\exp(-\beta_1 t')$$

Since workload $W_s$ is obtained by converting the sum of $W_1$, $W_2$, and $W_3$ to a "per minute value," it may be expressed finally as the following equation.

$$W_s = W_1 + W_2 + W_3 \times 10^{-7} \times \frac{60}{t_p} \text{ (J/min)} \quad (167)$$

The significance of displaying cardiac workload, in addition to systolic and diastolic pressure values at the proximal portion of the aorta, as explained above is as follows.

Namely, in the conventional sphygmomanometer, blood pressure is measured at the periphery of the arterial system, such as at the upper arm, radius artery or the like, and is therefore an indirect measurement of the load on the heart. However, changes in the load on the heart may not always be reflected in peripheral blood pressure values. Accordingly, using the periphery of the arterial system to interpret load on the heart cannot be viewed as a method of absolute accuracy.

Accordingly, in the present invention, emphasis is placed on the importance of using blood pressure waveforms at the center of the arterial system to view cardiac load, with the blood,pressure waveform of the proximal portion of the aorta (i.e., the center of the arterial system) estimated from pulse waveforms measured at the periphery. If the systolic and diastolic pressure values at the proximal portion of the aorta are then calculated from the estimated pressure waveform at the aorta, then these blood pressure values become indicators which directly show the load on the heart.

By obtaining cardiac workload as described above based on the pressure waveform at the aorta, it is possible to provide the systolic and diastolic pressure values at the proximal portion of the aorta as other useful indicators of cardiac load. Therefore, an explanation of the usefulness of cardiac load will now be explained using examples.

First, the case will be considered in which a hypertensive agent is administered to a patient to treat high blood pressure. Ordinarily, if the drug is effective, a change will be noted in the systolic and diastolic pressure values which are measured at the radius artery. However, even if no change is observed in the systolic and diastolic pressure values, it is still possible that the agent is having an effect in easing the load on the heart. This is because it is not absolutely essential that a hypertensive agent reduce the blood pressure at the radius artery, but rather, the agent's function is sufficient if it reduces the load on the heart somewhere along the arterial system. Thus, even if no marked change is observed in the blood pressure values at the periphery of the arterial system, such as at the radius artery, it is possible to know the actual load on the heart by calculating cardiac workload which is obtained from the blood pressure waveform at the proximal portion of the aorta.

However, while this type of change in the load on the heart may be observed by closely examining the blood pressure waveform at the proximal portion of the aorta, it is possible to quantitatively express very small changes in the waveform by calculating the cardiac workload. Accordingly, by obtaining cardiac workload and displaying it along with systolic and diastolic pressure values, it is possible to carry out an even more precise evaluation of a treatment method employing a hypertensive agent.

The results of calculating cardiac workload for each of the Type I through Type III pulse waveforms are shown in FIGS. 22 through 24.

<Modifications>

The present invention is not limited to the above-described embodiments, but rather a variety of modifications such as those below are also possible. For example, a modification may be considered in which the circulatory state parameters are determined without carrying out a measurement of stroke volume SV.

Figure 15:
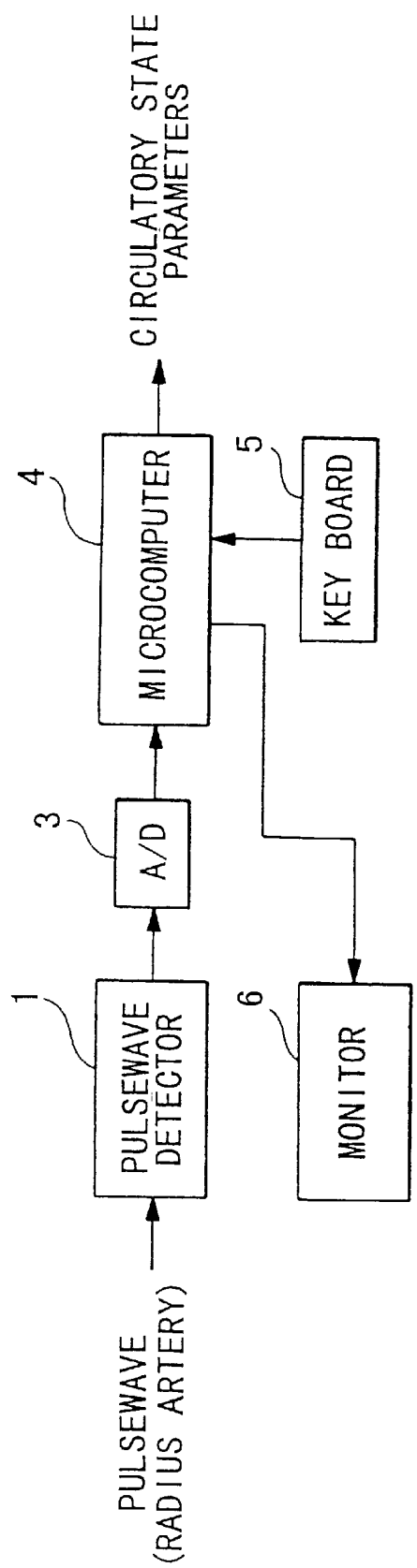
FIG. 15 is a block diagram showing the structure of a pulsewave analysis device according to another embodiment of the present invention.

Namely, from among the circulatory state parameters in this embodiment, inductance L is defined as a fixed value, and the values of the other parameters are calculated based only on the waveform of the pulsewave measured at the test subject's radius artery. In this case, as shown in FIG. 15, it is possible to omit stroke-volume measurer 2, which one of the essential elements in the structure shown in FIG. 1. Accordingly, as shown in FIG. 16, when carrying out measurements in this embodiment, cuff S1, which is required for the measuring arrangement shown in FIG. 2, is not necessary.

Figure 17:
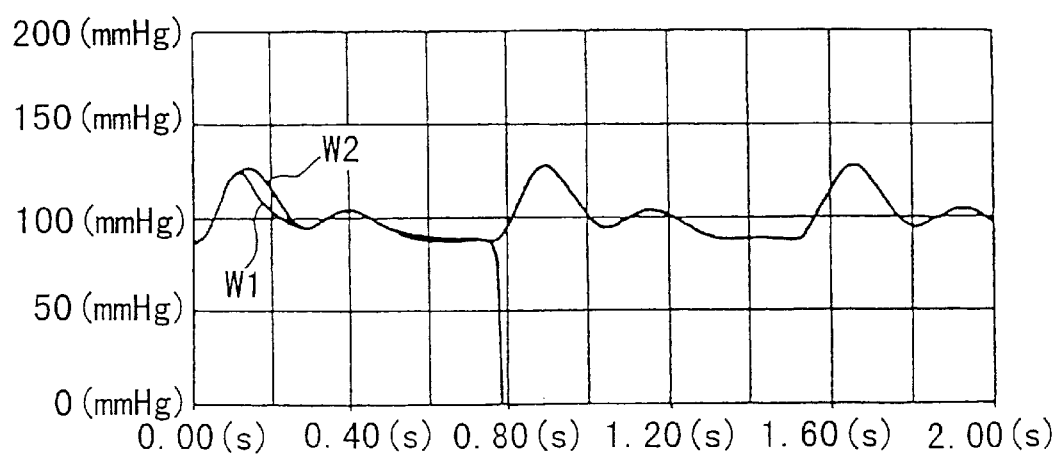
FIG. 17 is a diagram showing the display of the superimposition of the measured and calculated-waveforms of the radius artery, which is displayed by output device 6.

However, when the value of inductance L is defined as a fixed value, the accuracy of the obtained circulatory state parameters falls as compared to a method employing the actual measured value of stroke volume. Thus, in order to compensate for this fact, the waveform W1 of the radius artery obtained by measurement (i.e., measured waveform) and the waveform W2 of the radius artery obtained by calculation (i.e., calculated waveform) are superimposed and displayed on output device 6, as shown in FIG. 17. To begin with, the value of inductance L is defined as the aforementioned fixed value, and a calculated waveform W2 is obtained. This waveform is displayed on output device 6 and the degree of coincidence with the measured waveform W1 is observed. Next, the diagnostician determines a suitable value which is different from the fixed value to be inductance L. A calculated waveform W2 is again obtained, and the degree of coincidence with measured waveform W1 is observed on output device 6. Next, the diagnostician suitably determines a number of values for inductance L in the same manner as described above, determines calculated waveforms W2 for each of these inductance L values, and compares each of the calculated waveforms W2 with the measured waveform W1 on output device 6. One waveform is selected from among the calculated waveforms W2 which best matches measured waveform W1, and the value of the associated inductance L at that time is determined to be the optimal value.

Additionally, note that when modeling the pressure waveform at the proximal portion of the aorta, a squared-off waveform may be employed in place of the triangular waveforms described above. In this case, a waveform results which more closely approximately the actual pressure waveform than where approximating using triangular waves. As a result, it is possible to calculate even more accurate circulatory state parameters.

Figure 16:
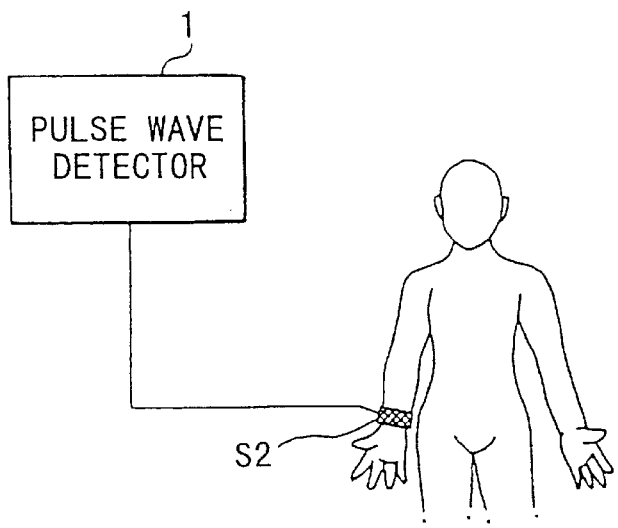
FIG. 16 is a diagram showing the conditions under which measurements employing a pulsewave detector 1 were conducted in this embodiment.

Further, the site of measurement of the pulsewave or stroke volume is not limited to those shown in FIGS. 2 and 16 Rather, any site on the test subject's body may be used. Namely, in the preceding embodiment, cuff S1 was affixed to the upper arm of the test subject, however, it may be preferable not to employ a cuff if the convenience of the test subject is an issue.

Figure 18:
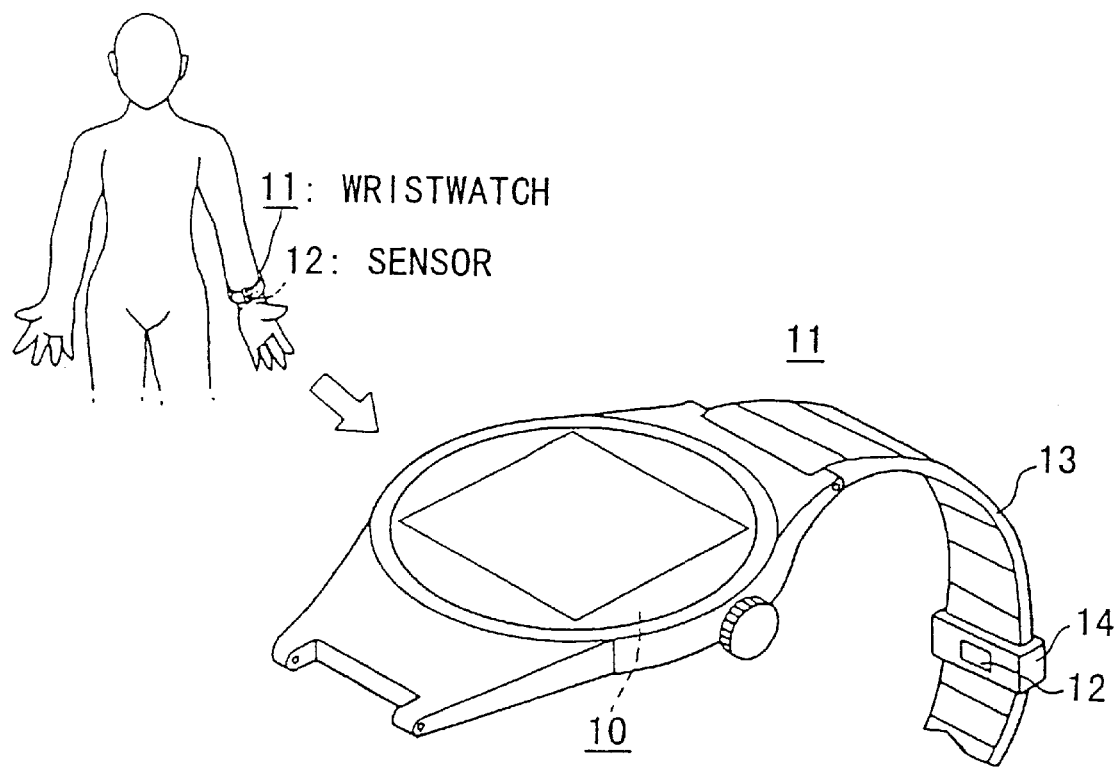
FIG. 18 is a squint view of the attachment of a sensor 12 to band 13 of a wristwatch 11, wherein the compositional elements 10 of the pulse wave analyzer, excluding sensor 12, are housed in wristwatch 11.

Therefore, as one example, an arrangement may be considered in which both the radius pulsewave and the stroke volume are measured at the wrist. In this type of design, as shown in FIG. 18, a sensor 12 consisting of a sensor for measuring blood pressure and a sensor for measuring stoke volume are attached to a belt 13 of a wristwatch 11. At the same time, structural elements 10 other than sensor 12 of a pulsewave analysis device are housed in the main body of wristwatch 11. As shown in the figure, sensor 12 is attached in a freely sliding manner to belt 13 via a fastener 14. By fastening wristwatch 11 to the wrist of the test subject, the sensor presses against the radius artery under a suitable pressure.

Figure 19:
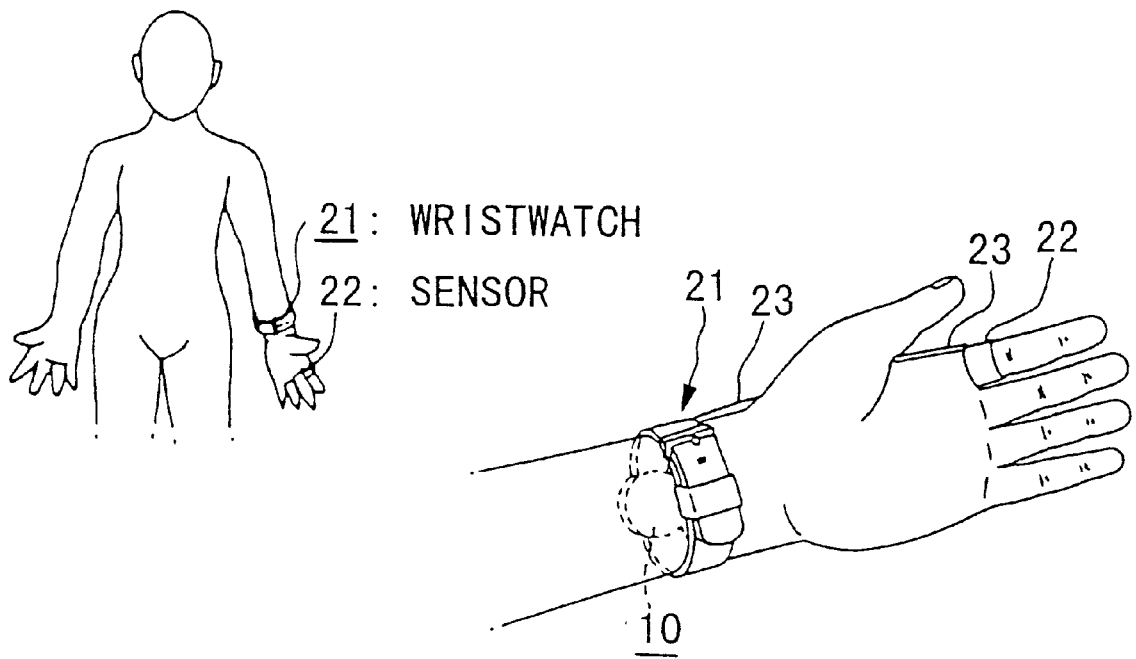
FIG. 19 is a squint view of the attachment of a sensor 22 to the base of a finger, wherein the compositional elements 10 of the pulse wave analyzer, excluding sensor 22, are housed in wristwatch 11.

In addition, another embodiment may be considered in which the pulsewave and stroke volume are measured at the finger. An example of the structure of a device according to this embodiment in shown in FIG. 19. As shown in this figure, a sensor 22 comprising a sensor for measuring blood pressure and a sensor for measuring stroke volume are attached to the base of a finger (the index finger in this figure). At the same time, structural elements 10 other than sensor 22 of the pulse wave analysis device are housed in wristwatch 21 and are attached to sensor 22 via lead wires 23,23.

Moreover, by combining these two embodiments, other arrangements may be realized such as one in which the stroke volume is measured at the wrist and the pulsewave is measured at the finger, or one in which the stroke volume is measured at the finger and the radius artery pulsewave is measured at the wrist.

As in the above-described cases, then, it is possible to realize a structure which does not employ a cuff, so that measurements can be carried out without wrapping an apparatus to the upper arm of the test subject. Thus, the burden on the test subject during measurement is reduced.

Figure 20:
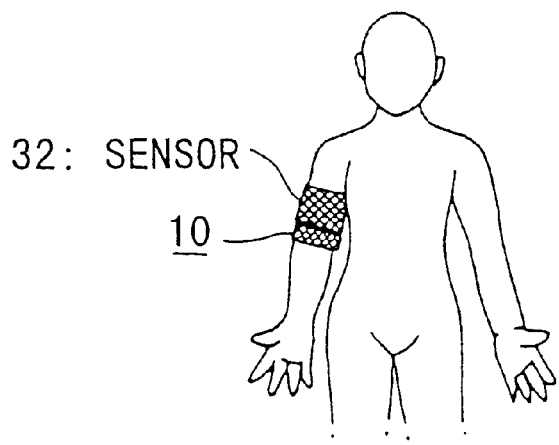
FIG. 20 is a structural diagram showing the attachment of sensor 32 and the compositional elements 10 of the pulse wave analyzer, excluding sensor 32, to the upper arm via a cuff.
Figure 21:
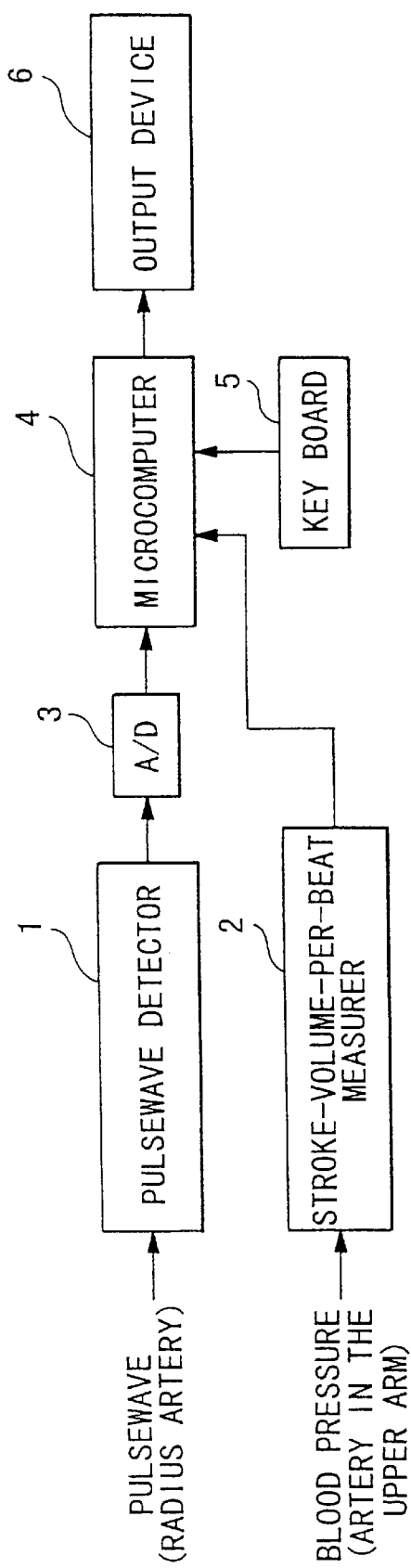
FIG. 21 is a block diagram showing the structure of a sphygmomanometer according to the second embodiment of the present invention.

On the other hand, a design such as shown in FIG. 20 may be considered which employs a cuff alone. As shown in this figure, a sensor 32 comprising a sensor for measuring blood pressure and a sensor for measuring stroke volume, and the structural components 10 other than sensor 32 of a pulsewave analysis device are affixed to the upper arm of a test subject by means of a cuff. Accordingly, a simpler structure as compared to that in FIG. 2 is realized.

In addition, in the preceding embodiments, the pulsewave was employed when calculating circulatory state parameters. However, the present invention is not limited thereto; rather other physiological conditions may of course be employed for the calculation of the circulatory state parameters.

What is claimed:

1. A device for measuring a physiological state in an organism having an arterial system extending from a center portion of the organism's body to a periphery thereof, said device comprising:
   measuring means for measuring the physiological state on the basis of a pulse wave detected at a periphery of the arterial system; and
   analysis means for calculating circulatory state parameters, including viscoelasticity of an aorta of the arterial system, based on the measured physiological state, to show a circulatory state of the arterial system from the center to the periphery.

2. A device according to claim 1, wherein the circulatory state parameters further include blood vessel resistance at the center of the arterial system due to blood viscosity, blood inertia at the center of the arterial system, blood vessel resistance at the periphery of the arterial system due to blood viscosity, and blood vessel viscoelasticity at the periphery of the arterial system.

3. A device according to claim 1, further comprising blood pressure calculating means for calculating a pressure waveform at the aorta based on the calculated circulatory state parameters.

4. A device according to claim 3, wherein the circulatory state parameters further include blood vessel resistance at the center of the arterial system due to blood viscosity, blood inertia at the center of the arterial system, blood vessel resistance at the periphery of the arterial system due to blood viscosity, and blood vessel viscoelasticity at the periphery of the arterial system.

* * * * *

UNITED STATES PATENT AND TRADEMARK OFFICE
CERTIFICATE OF CORRECTION

PATENT NO. : 6,331,159 B1
DATED : December 18, 2001
INVENTOR(S) : Kazuhiko Amano et al.

It is certified that error appears in the above-identified patent and that said Letters Patent is hereby corrected as shown below:

<u>Title page,</u>
Item [56], References Cited, OTHER PUBLICATIONS, add:
-- "Mathematical and Computer Modeling Of Physiological System", Page 87 and 106, published 1991 --
-- Hiroshi Yagi, *"Medical Electric Measurement"*, May 23, 1985, Sangyo Tosho K.K. pp. 32-36; Fig. 1 --
-- Jacob Kline, *"Handbook of Biomedical Engineering"*, Academic Press, 1988, pp. 623-624. --

U.S. PATENT DOCUMENTS, add:
-- 5,101,828   4/7/92    Welkowitz, et al. --
-- 5,103,831   4/14/92   Niwa --
-- 5,140,991   8/25/92   Niwa --
-- 5,152,297   10/6/92   Meister, et al. --
-- 5,533,511   7/9/96    Kaspari, et al. --
-- 5,730,137   3/24/98   Amano, et al. --
-- 5,830,131   11/3/98   Caro, et al. --

FOREIGN PATENT DOCUMENTS, add:
-- 0 386 620    9/12/90    EPO --
-- 0 664 102    7/26/65    EPO --
-- 3-501575     4/11/91    Japan --
-- 4-276234     10/1/92    Japan --
-- 6-205747     7/26/94    Japan --
-- 6-261870     9/20/94    Japan --
-- 6-505651     6/30/94    Japan --
-- 48-50583     7/17/73    Japan --
-- 58-216034    12/15/83   Japan --

Signed and Sealed this

Twenty-eighth Day of January, 2003

JAMES E. ROGAN
*Director of the United States Patent and Trademark Office*